(12) United States Patent
Genosar

(10) Patent No.: US 10,864,139 B2
(45) Date of Patent: Dec. 15, 2020

(54) ASEPTIC CARTRIDGE AND DISPENSER ARRANGEMENT

(71) Applicant: AKTIVAX, INC., Broomfield, CO (US)

(72) Inventor: Amir Genosar, Boulder, CO (US)

(73) Assignee: AKTIVAX, INC., Broomfield, CO (US)

(*) Notice: Subject to any disclaimer, the term of this patent is extended or adjusted under 35 U.S.C. 154(b) by 0 days.

(21) Appl. No.: 15/789,478

(22) Filed: Oct. 20, 2017

(65) Prior Publication Data

US 2018/0235840 A1 Aug. 23, 2018

Related U.S. Application Data

(63) Continuation of application No. 13/992,191, filed as application No. PCT/US2011/063624 on Dec. 7, 2011, now Pat. No. 9,820,913.

(Continued)

(51) Int. Cl.
| | |
|---|---|
| *A61J 1/20* | (2006.01) |
| *A61M 5/28* | (2006.01) |
| *A61M 5/24* | (2006.01) |
| *B65D 75/36* | (2006.01) |
| *A61J 1/06* | (2006.01) |

(52) U.S. Cl.
CPC .......... *A61J 1/2093* (2013.01); *A61J 1/2096* (2013.01); *A61M 5/2448* (2013.01); *A61M 5/2455* (2013.01); *A61M 5/28* (2013.01); *A61M 5/284* (2013.01); *A61M 5/285* (2013.01); *B65D 75/367* (2013.01); *B65D 75/368* (2013.01); *A61J 1/067* (2013.01); *A61J 1/201* (2015.05);

(Continued)

(58) Field of Classification Search
CPC ...... A61J 1/2093; A61J 1/2096; A61J 1/2024; A61J 1/2027; A61J 1/067; B65D 75/367; B65D 75/368

See application file for complete search history.

(56) References Cited

U.S. PATENT DOCUMENTS

| | | |
|---|---|---|
| 5,176,634 A | 1/1993 | Smith et al. |
| 5,374,256 A | 12/1994 | Kriesel |

(Continued)

FOREIGN PATENT DOCUMENTS

| | | |
|---|---|---|
| EP | 1308149 A2 | 5/2003 |
| JP | 2006230467 | 7/2006 |
| WO | 2010081174 A2 | 7/2010 |

OTHER PUBLICATIONS

Extended European Search Report, European Patent Application No. 11847715.7, dated Aug. 12, 2015, 6 pages.

(Continued)

*Primary Examiner* — Timothy L Maust
*Assistant Examiner* — Jason K Niesz
(74) *Attorney, Agent, or Firm* — Holzer Patel Drennan

(57) ABSTRACT

A cartridge for use with a beneficial agent delivery device having a fillable reservoir. The cartridge includes a reconstitution, unit dose package having first and second compartments, and a fitment. The first compartment contains at least a first constintuent of the beneficial agent. The second compartment contains at least a second constituent of the beneficial agent. The fitment is disposed on the package for interfacing the package to the fillable reservoir.

15 Claims, 27 Drawing Sheets

Related U.S. Application Data

(60) Provisional application No. 61/533,194, filed on Sep. 10, 2011, provisional application No. 61/523,422, filed on Aug. 15, 2011, provisional application No. 61/487,121, filed on May 17, 2011, provisional application No. 61/467,359, filed on Mar. 24, 2011, provisional application No. 61/433,493, filed on Jan. 17, 2011, provisional application No. 61/419,892, filed on Dec. 6, 2010.

(52) U.S. Cl.
CPC ......... *A61J 1/2024* (2015.05); *B65D 2221/00* (2013.01)

(56) References Cited

U.S. PATENT DOCUMENTS

| | | | |
|---|---|---|---|
| 5,431,496 A | 7/1995 | Balteau et al. | |
| 5,462,526 A | 10/1995 | Barney et al. | |
| 5,611,782 A * | 3/1997 | Haedt .................. | A61J 1/2096 604/198 |
| 5,899,244 A | 5/1999 | Nish et al. | |
| 5,928,213 A | 7/1999 | Barney et al. | |
| 5,944,709 A * | 8/1999 | Barney .................. | A61J 1/10 206/219 |
| 6,231,559 B1 * | 5/2001 | Loretti ................. | A61J 1/2093 604/410 |
| 6,231,599 B1 | 5/2001 | Loretti | |
| 6,585,693 B1 * | 7/2003 | Dischler ............... | A61M 5/282 604/171 |
| 2001/0056272 A1 | 12/2001 | Yagi et al. | |
| 2003/0080129 A1 | 5/2003 | Takimoto et al. | |
| 2004/0188281 A1 * | 9/2004 | Iwasa .................... | A61J 1/1487 206/219 |
| 2006/0191594 A1 | 8/2006 | Py | |
| 2007/0027437 A1 | 2/2007 | Burg et al. | |
| 2007/0075714 A1 | 4/2007 | Dollinger et al. | |
| 2007/0261974 A1 | 11/2007 | Balteau et al. | |
| 2008/0017543 A1 | 1/2008 | Pahlberg et al. | |
| 2008/0044606 A1 | 2/2008 | Omori et al. | |
| 2008/0234654 A1 | 9/2008 | McCarthy et al. | |
| 2008/0283439 A1 | 11/2008 | Sullivan et al. | |
| 2009/0032489 A1 | 2/2009 | Moy et al. | |
| 2009/0171311 A1 | 7/2009 | Genosar et al. | |
| 2009/0204071 A1 | 8/2009 | Grant et al. | |
| 2010/0298804 A1 | 11/2010 | Inoue et al. | |
| 2012/0330280 A1 | 12/2012 | Reynolds et al. | |
| 2013/0012912 A1 | 1/2013 | Suzuki et al. | |
| 2013/0190681 A1 | 7/2013 | Jansson et al. | |
| 2013/0327672 A1 | 12/2013 | Kurowski et al. | |
| 2014/0008366 A1 | 1/2014 | Genosar | |
| 2014/0053952 A1 | 2/2014 | Genosar | |

OTHER PUBLICATIONS

Korean Intellectual Property Office, International Search Report—PCT/US2011/063624—dated Jun. 26, 2012, 3 pp.
European Application No. 11847715.7, Communication Pursuant to Article 94(3) EPC, Nov. 13, 2017, 5 pages.

* cited by examiner

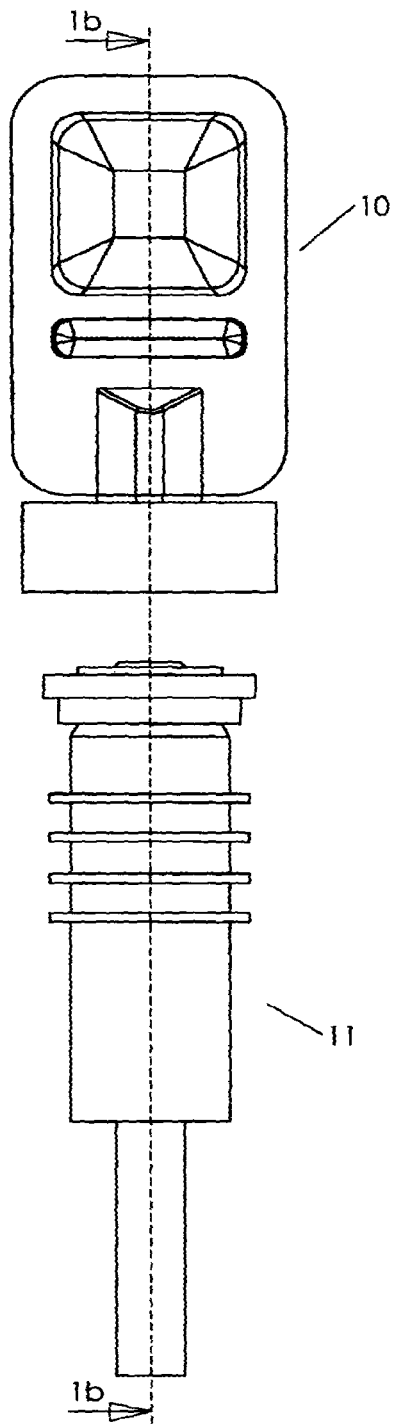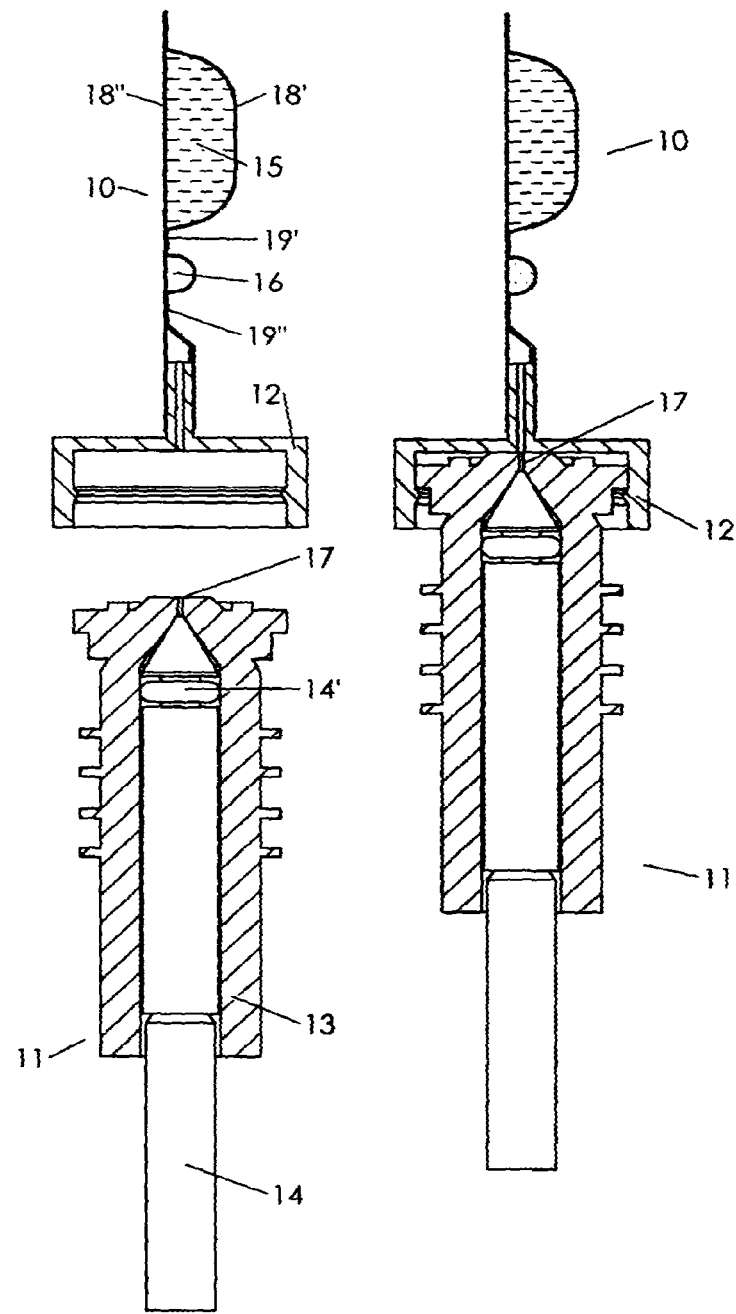
Figure 1a    Figure 1b    Figure 1c

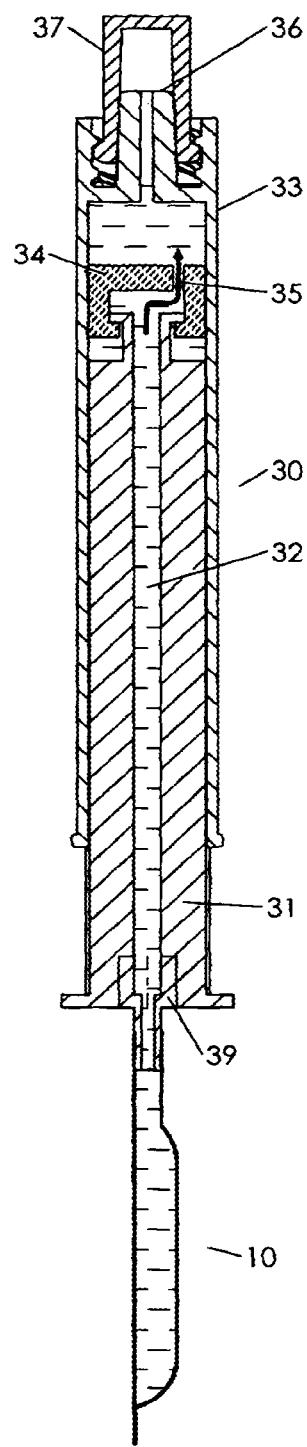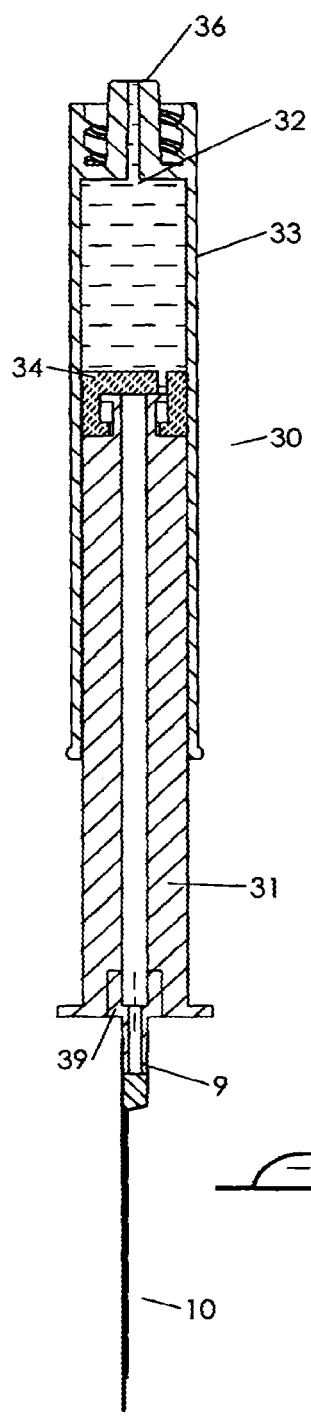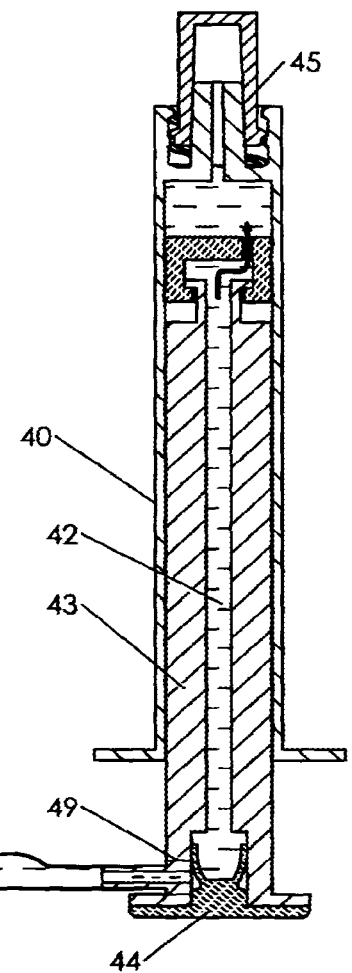
Figure 3a
Figure 3b
Figure 4

ASEPTIC CARTRIDGE AND DISPENSER ARRANGEMENT

TECHNICAL FIELD

The present disclosure preferably, but without limitation, generally pertains to disposable cartridges for use with drug delivery devices, and more specifically pertains to aseptic mixing cartridges for drug delivery devices.

BACKGROUND

Medications, and in particular injectable medications, need to be stored sterile in aseptic commercial packages until the time of use. Some medications are stored in prefilled single dose dispensing devices such as prefilled syringes, for example the prefilled syringes from Vetter (Ravensburg, Germany). Yet most of injectable medication are stored in aseptic packages and are transferred to a dispensing device (i.e. drug delivery device) shortly before use. The term dispensing device include without limitation hypodermic syringes, micro-needle syringes, micro-pumps, auto-injectors, jet injectors, topical dispensers, intradermal delivery devices, patch pumps, ear dispensers, oral dispensers, eye droppers, auto-injectors, infusers, or any other type of drug delivery device.

Several aseptic packages for storing injectable medications are commercially available. Perhaps the most common aseptic package for injectable products is glass vials. Some medications are stored in separate components that are mixed just prior to use. Often this is done to improve the medication's stability or to extend the medication's shelf life. In one example the medication is a vaccine that is kept dry in one vial to extend the vaccine thermo stability; and a companion vial stores a dilutent that is dispensed to the vaccine vial via a syringe and needle prior to injection. In another example the medication is a vaccine where one vial stored the formulated antigen and the second vial stores an adjuvant.

However, there are several drawbacks with this prior art: (a) these packages are many time costly and economically impractical to many injectable drugs such as vaccines; (b) where mixing of the medication components is required the process is complex and error prone; and (c) the transfer of the medication or its components from one container to another or to the dispensing device is done in a non-sterile field and is prone to contamination risks.

U.S. Pat. No. 7,879,018 discloses one of several commercial and patented kits for mixing an injectable dose. Here again the limitation of the disclosure is the dependency on vials and the cost and complexities associated with this type of glass primary containers.

Several commercial products and patents disclose a flexible package made from film or foils in which a product can be stored in an aseptic manner until the time of use. Some of these products and patents further disclose a dispensing port communicating with the product in the dispensing package. In some cases a rupturable barrier is presented between said port and the product to enhance the integrity of the package until the time of use. In some cases these flexible packages comprise at least two product compartments that are mergeable prior to use to allow the substances from the different compartments to mix and form the dispensable product. These packages are sometimes referred to as pouches or sachet. One disadvantage of pouch packages is that it is relatively challenging to efficiently express the entire content of the package. This is due to the dimensional ratio of these packages where the length and width are typically significantly larger than the perpendicular protrusion to their plane. This ratio is an inherent limitation of the way pouch/sachet packages are formed. Pouches and sachets are formed from one or more flat film or foil (together "web") that is sealed along its edges to form one or more receptacle. The pouch is filled during or post the receptacle formation and then sealed to keep the product aseptically packaged.

When operated directly with the palm, one limitation of these relatively shallow packages is that, when dispensing, the thumb of the operator very quickly bring two opposite walls of the package in contact at which point the dispensing is halted. Sophisticated peristaltic action or folding of the package would typically be necessary to express additional product from the package. In some arrangements, the flexible package is depressed with a compression panel to cause the content to expel. In these arrangements it is beneficial to operate the compression panel to depress a smaller contact surface of the product compartment, and hence allow developing more pressure. It is therefore advantageous to create a flexible dispensing package where the footprint of the content compartment is relatively small and the ratio between the sealed area and the dimension of the package perpendicular to that surface is smaller.

In some applications, the deliverable medication requires a thorough mix of at least two substances prior to injection. In one example, a simple method is required to prepare a highly viscous water in oil (W/O) at point of use. At present, an emulsion is prepared by hand by mixing separate oil and water components back and forth via three-way stopcock or a narrow tube connecting two syringes. The method is somewhat time consuming and often inconsistent. Connectors that have a porous membrane inside the syringes have been developed to provide more effective emulsion but at the expense of needing stronger pushing force particularly when pore diameter is decreased in order to shorten preparation time. In addition the increased number of assembly and dismantle steps enhance the risks of operation errors and contamination of the deliverable dose.

SUMMARY

At least some aspects of the present disclosure overcome the disadvantages and limitations of the prior art by providing, for example, a low cost, simple and easy to use cartridge. The cartridge, in certain configurations, allows for aseptic mixing and filling of dispensers and in particular drug delivery injectors.

In some arrangement of the present disclosure, the package is made from at least one web material wherein a first wall and a second wall of said web material are joined together along a boundary line of a compartment. In some arrangements the web material is pre-formed such that a relatively large volume of the compartment is achieved with a relatively smaller sealing footprint. This pre-formed package may reduce the overall dimensions of the package and improve storage and transportation efficiencies.

According to one arrangement of the present disclosure, a cartridge having a thin and flexible wall package comprises at least a first constituent compartment and a fitment for connecting the cartridge to a filling port of a dispenser. The fitment is attached to the package in a fluid-tight fashion. The fitment may be attached to the filling port of the dispenser by one of the means, but is not limited to a Luer connector, a Luer lock connector, a press-fit connector, a snap-on connector, a snap, or a screw on cap.

In some arrangements, at least one cavity is pre-formed in at least one of the web walls of the package, which provides a portion of at least one product compartment of the package. This configuration allows a smaller ratio of the sealed area (footprint) of the compartment and the dimension of the compartment perpendicular to the sealed area (the swelling of the compartment), for storing the same volume of product. This configuration also permits a smaller footprint of the compartment than what would be required with a sachet/ pouch package with a similar product volume. Forming of the web may be performed by one of the means known in the art, appropriate to the properties of the particular web material including, for example, thermoforming, cold forming, forming with preheat, plug-assist, pressure forming, vacuum forming, and a combination of the above.

In some arrangements, the package is constructed from a thin wall using one of the forms known in the art including, for example, a blister, a pouch, a sachet, a blow-molded container or an extruded container. In some arrangements, the package may have more than one compartment for storing a number of substances that need to be mixed prior to delivery to a subject to form the dispensable product. The compartments may be separated by a weak seal that can be broken by compressing at least one of the compartments to exceed a threshold pressure of at least one of the substances that will cause the weak seal to separate (e.g., rupture or peel) and allow the substances to mix. The package further comprises an interface to the dispenser.

In some arrangements, the product is transferred from the cartridge to the dispensing device. In some arrangements, the cartridge is replaced in the dispensing device. In some embodiments, the cartridge is connected to the dispenser in an aseptic fashion at the manufacturing stage, thus no integration steps of the cartridge and dispenser are required by the user. This arrangement reduces the possibility for user error or contamination of the device or the deliverable product as it avoids exposure to a non-sterile conditions prior or during the dispenser filling/loading process. In another arrangement, the cartridge is stored separately from the dispensing device (i.e. syringe, injector, etc.) until the time of use. This arrangement may be advantageous where the drug needs to be stored and transported in a controlled environment, such as in controlled temperature refrigeration, and where packaging efficiency is important. This arrangement may also be advantageous to increase logistic and user flexibility to select different sources and fashion of the delivery device.

In some arrangements, the dispensing device may be an injector. The term injector may refer to various dispensing products including micro-infusion pumps or reservoirs such as, for example, pen injectors, reservoir assemblies, syringes, needle-free injectors, drug delivery devices in general, patch devices, etc. More generally, the cartridge of the present disclosure is applicable for dispensing devices including, for example, ocular oral or ear droppers, spray or foam dispensers, topical applicators, and inhaler devices.

In another arrangement, a static mixer is disposed at the interface between the cartridge device and the drug delivery device to enhance the mixing and homogeneousness of the deliverable product. An example of a static mixer is taught in U.S. Pat. No. 4,538,920, which is incorporated herein in its entirety by this reference. In some arrangements the static mixer is constructed as a pattern of passageways formed between the walls of the flexible walls by welding and performing a designated areas of the walls. The static mixer may be merely a narrow nozzle, or a porous component accommodated in the flow passageway between the cartridge and the delivery device. In one arrangement, the static mixer is disposed in the cartridge port. In one arrangement, the cartridge comprises more than one compartment holding different substances, which are merged prior to transferring the content to the delivery device, and the static mixer enhances the mixing of the substances as they are transferred to the delivery device.

In some arrangements, the mixture may be transferred back and forth between the cartridge and delivery device to further mix the substances. In some arrangements, at least one substance is stored in the cartridge and at least one substance is stored in the delivery device and the substances are transferred back and forth between the two to mix the substances. In one arrangement, the cartridge comprises at least a first and a second compartment and at least one static mixer is disposed between the first compartment and the second compartment. Mixing may be enhanced by transferring the substances/mixture from one compartment to the other compartment. At least one compression panel or an arrangement of compression panels may be operated with the cartridge to facilitate the transfer of substances across the static mixer.

The present disclosure also relates to arrangements and methods facilitating efficient cartridge manufacturing and filling. In one arrangement, a compartment of the package is filled with fluid. The compartment is formed sealed leaving a designated passageway open that leads to a port through which the fluid is introduced and the air is evacuated. Separate passageway for gas evacuation may be incorporated. The passageway may be constructed such that the fluid entering the port glides along the wall of the package, hence avoiding jetting, and minimizing foaming or air bubble formation, thus allowing increased filling rate.

In another arrangement, a liquid substance is frozen prior to filling and is introduced into the package in a solid form. The temperature around the package and the heat transfer to the package during the filling process is controlled such that the frozen liquid remains substantially solid until the compartment is sealed. The frozen liquid substance doze may be inspected in that form prior or during filling. This filling arrangement and method enhances the filling speed, and the substance inspection capability. In one arrangement, a dry powder substance has to be filled into the cartridge compartment. To facilitate proper filling of the powder, the powder is slightly compressed to form a loosely aggregated tablet and is filled in that form into the compartment of the package. The tablet may be inspected prior or during filling to the cartridge. In one arrangement, after the tablet has been sealed in the compartment, the compartment is externally manipulated to de agglomerate the tablet thus improving the substance solubility at the time of mixing with a diluent. The external manipulation may be at least one of, but not limited to, compression of the compartment, vibration including, for example, ultrasonic vibration, radio frequency vibration, acoustic vibration, applying mechanical impact to the compartment, and exposure to high or low temperatures.

The present disclosure further relates to arrangements that enhance the barrier properties of the package by including a high barrier peelable opaque wall layer. The peelable high barrier layer may include an aluminum laminate that provides the benefits of light blocking, and close to absolute moisture and oxygen barrier. In order to have a visual inspection of the content of the cartridge prior to use, the high barrier layer is peeled from at least a portion of the package, exposing a substantially see-through wall. In one arrangement the peelable layer is an integral layer of the web material from which the package is made. In another arrangement the peelable layer is applied to the see-through wall during the cartridge manufacturing process. In one arrangement the peelable layer is flat. In another arrangement the peelable layer is pre-formed to accommodate the form of the substance or compartment that it is protecting. In one arrangement the peelable layer comprise a registered adhesive coating selectively applied to the sealing circumference of the peelable layer. In one arrangement the cartridge is in the fashion of a flexible clear-wall tube, and the peelable layer is arranged to wrap around the tube.

Another aspect of the present disclosure relates to a cartridge for use with a beneficial agent delivery device having a fillable reservoir. The cartridge includes a reconstitution, unit dose package having first and second compartments, and a fitment. The first compartment contains at least a first constituent of the beneficial agent. The second compartment contains at least a second constituent of the beneficial agent. The fitment is disposed on the package for interfacing the package to the fillable reservoir.

Another aspect of the present disclosure relates to an aseptic cartridge for use with a beneficial agent delivery device having a fillable reservoir. The cartridge includes a package having at least a first compartment and a fitment. The first compartment contains at least one constituent of the beneficial agent, and the package is at least partially defined by a pre-formed flexible wall. The fitment is disposed on the package for interfacing the package in fluid communication with the fillable reservoir.

A further aspect of the present disclosure relates to a cartridge for use with a beneficial agent delivery device having a fillable reservoir. The cartridge includes a backing and a package assembly. The package assembly includes at least a first compartment and a fitment. The first compartment contains at least one constituent of the beneficial agent and is at least partially defined by a flexible wall. The fitment is disposed on said package for interfacing said package in fluid communication with the fillable reservoir.

Another aspect of the present disclosure relates to a cartridge for use with a beneficial agent delivery device having a fillable reservoir. The cartridge includes a package having at least a first compartment, a fitment, and a coupler. The first compartment contains at least one constituent of the beneficial agent. The fitment is disposed on the package. The coupler is joined to the fitment for interfacing the package in fluid communication with the fillable reservoir.

A further aspect relates to a cartridge for use with a beneficial agent delivery device having a fillable reservoir. The cartridge includes a unit dose package containing all of the beneficial agent or all constituents thereof. The cartridge includes at least a first compartment containing all of said beneficial agent or at least one constituent thereof, wherein the first compartment is at least partially defined by a flexible wall. The cartridge also includes a fitment disposed on the package for interfacing the package in fluid communication with the fillable reservoir.

A further aspect relates to a pre-filled cap for enclosing an administration portion of a unit dose beneficial agent delivery device comprising a unitary reservoir. The pre-filled cap includes at least a first compartment containing at least one constituent of the beneficial agent, and a fluid passageway for communicating said first compartment with said administration portion.

A beneficial agent unit dose dispenser in accordance with the present disclosure includes a delivery device and a cartridge. The delivery device has a fillable, unit dose reservoir and at least one port in communication with said fillable reservoir. The cartridge is aseptically joined to the delivery device and includes a unit dose package. The unit dose package includes at least a first compartment, a fitment, and an openable seal. The first compartment contains at least one constituent of the beneficial agent, and the package is at least partially defined by a flexible wall. The fitment is joined with the unit dose package and interfaces the unit dose package to the delivery device. The openable seal is disposed between the first compartment and the reservoir.

Another aspect of the present disclosure relates to a pre-filled syringe for dispensing a beneficial agent. The pre-filled syringe includes a piston assembly, a fillable barrel comprising an administration portion, and a pre-filled cartridge comprising at least a first compartment containing at least a first constituent of the beneficial agent, and a flow passageway for communicating contents said first compartment to said barrel.

A further aspect of the present disclosure relates to a cap for an administration portion of a delivery device. The cap comprises a fluid passageway, a proximal end configured to communicate with said administration portion, and a distal end.

An example method in accordance with the present disclosure relates to a method for forming a pre-filled package of a beneficial agent. The method includes providing a webbing having a first side and a second side joined together to form a boundary of at least a first constituent compartment therebetween, forming a frangible seal along at least a portion of said boundary, forming a permanent seal such that said permanent seal overlaps at least some of said frangible seal to create an overlapped portion having substantially the same sealing properties as said permanent seal, and filling the first constituent compartment.

Another example method in accordance with the present disclosure relates to a method of forming a pre-filled package of a beneficial agent. The method includes forming a gas-filled compartment for the beneficial agent, forming a filling compartment having a filling port communicating with the gas-filled compartment via a first sealable channel, and forming an exhaust compartment having an exhaust port communicating with said gas-filled compartment via a second sealable channel. The method also includes coupling a source of at least a first constituent of the beneficial agent with said filling port in a fluid tight fashion, filling said gas-filled compartment from said source via said filling channel while evacuating gas through said exhaust port, and sealing said first sealable channel and said filling channel.

A further method incordance with the present disclosure relates to a method of producing a unit-dose delivery device for a beneficial agent that includes receiving an assembled delivery device, receiving a pre-filled, aseptically sealed cartridge which has been prefilled with at least a first constitutent of the beneficial agent, and integrating said delivery device and said aseptically sealed cartridge.

Another example method relates to filling a package with a unit-dose of beneficial agent in a liquid state. The method includes freezing a metered unit-dose of said beneficial agent in a mold to create a frozen dose, placing the frozen dose in a semi-finished compartment, and sealing said compartment.

Another example method relates to filling a package with a metered dose of at least a first constituent of a beneficial agent in a flowable solid material form. The method includes metering a dose of the first constituent, compressing said metered dose enough to form a unitary body, placing said unitary body in a semi-finished package, sealing the package, and directing energy at the unitary dose through a wall of the package to transform the unitary dose into a particulate.

The applications of the present invention are not limited to drug delivery, which is provided herein by way of example. The teachings described herein can be applied to dispensing devices in other areas such as, for example, glue dispensing, chemicals dispensing, etc. The present disclosure provides various configurations for accomplishing this.

BRIEF DESCRIPTION OF THE DRAWINGS

FIGS. 1a to 1f illustrate an injector cartridge assembly with a blister package associated with its cap, which can be employed to various configurations;

FIGS. 3a and 3b illustrate a prefilled syringe assembly with a package associated with its piston's stem, and extending axially from it, which can be employed to various configurations;

FIG. 4 illustrates a syringe assembly with a blister package associated with its stem, and extending laterally from it, which can be employed to various configurations;

FIGS. 3a and 3b number 39 is showing a fitment

FIG. 4 number 49 is showing a fitment

FIG. 15 the second compartment is hermetically sealed empty and can be filled via filling arrangement 152 as will be described in Figure

DETAILED DESCRIPTION

Figure 1D:
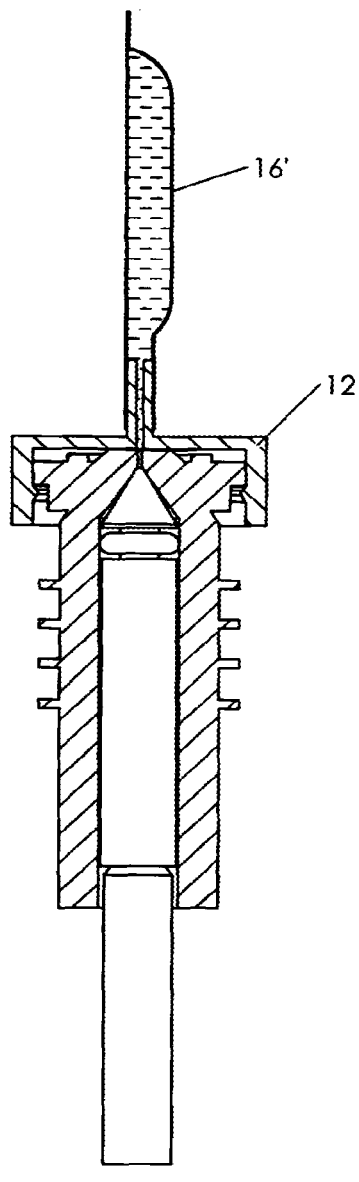

FIG. 1a shows an arrangement of an injector 11 and a cartridge 10. The figure provides the section line for the section view of FIG. 1b. FIG. 1b illustrates a section view of an injector assembly 11 and a cartridge 10. The injector 11 comprises a body 13 in a form of a barrel and a piston 14 disposed in said body and is moveable along the axis of the body between a forward, empty state, and a retracted, filled states. The piston 14 further comprises an O-ring seal 14', providing a fluid tight seal between the body and the piston, and defining a compartment in front of said piston for receiving a fluid dose. The compartment is shown at the emptied state, where the piston is advanced to the forward most position in the body 13. A jet nozzle 17, at the front of the body provides a port for filling a fluid dose to the injector 11, and for hypodermically delivering said dose to a subject in a needle-free jet injection fashion.

The cartridge 10 comprises a first thin wall 18', formed to provide two cavities; and a second thin wall 18" which seals against the first thin wall 18' to define a first sealed compartment 15 and a second sealed compartment 16. A fitment 12 is attached to the package between the first wall 18' and the second wall 18". The fitment 12 is structured to engage with the front of the injector body 13. A first frangible seal section 19', separates between the first compartment 15 and the second compartment 16, and is peelable by a defined threshold force. A second frangible seal 19" separates between the second compartment 16 and the fitment 12, and is peelable at a defined threshold peeling force. The thin walls 18' and 18" may be made from a type of film or foil (together referred to as "web" or "web material") including extruded web, blown web, cast web, multilayer web, laminated web, coated web, webs including metalized layers such as aluminum layer, webs including metal oxide layers such as alumina or silica, webs including high barrier layer including Cyclic Olefin Polymer (COP), Cyclic Olefin Copolymer (COC), polychlorotrifluorocthylenc (PCTFE), Ethylene Vinyl Alcohol (EVOH). The inner adhesive layer of the web material may be made from Olefin ionomers, Ethylene-vinyl acetate (EVA) or other materials.

It may be advantageous to incorporate an adhesive layer to the web that have a controlled peeling force such that designated areas of the circumferential seal around the compartment would have lower peeling force than others, thus limiting the areas that will be ruptured when a threshold peeling force is applied to the seal area between the first wall 18' and the second wall 18". One such adhesive layer is the ionomer bland brand EZ Peel® (Bemis, Neenah, Wis.) which produces a peelable seal at sealing temperature of 130° C., and a permanent non-peelable seal at sealing temperature of 170° C., thus allowing a good control of the sealing properties by performing a two stage welding process at different temperatures.

Another approach to accomplishing a desired sealing force pattern between the first wall 18' and the second wall 18" is to have the inner layer of the web made with a selective adhesive pattern of at least two adhesive types with different peeling strength. The fitment 12 may be made from an olefin polymer that will have good adhesion to the inner layer of the web. In some arrangements the fitment is attached to the outer side of one of the first wall 18' or the second wall 18", and a through hole in the web communicates the content of the cartridge 10 and the fitment 12. In this arrangement the fitment material should be compatible for attachment to the web's outer layer material. The cartridge compartments 15, 16 may contain various substances. In one embodiment, the first compartment 15 contains a dilutent and the second compartment 16 contains a beneficial agent in dry format, and the content of the two compartments needs to be mixed to form a dispensable product dose. In one embodiment, the first compartment 15 contains a dilutent such as saline or water for injection, and the second compartment contains a vaccine in dry powder format.

The content of the first compartment 15 and the second compartment 16 may be in various forms including liquid, gel, paste, slurry, solid, granules, pellets, flowable powder, compressed powder, a cake, a lyophilized cake, or other forms known in the art. When the first compartment contains a fluidic material, the first frangible seal 19' may be separated by depressing the first compartment 15 and pressurizing said content, thereby applying force to the first frangible seal 19' and peeling apart the seal, creating a joined compartment between compartment 15 and compartment 16, and allowing the content of the two compartments to mix. The second frangible seal 19" may be ruptured by depressing the joined compartment and pressurizing its content there by causing a peeling force to the second frangible seal 19".

FIG. 1c shows the cartridge 10 mounted on to the injector 11. The fitment 12 is engaged with the front end of injector body 13, preferably creating an aseptic zone within the fitment area. A passageway of fitment 12 and the injector nozzle 17 are in fluid communication. For parenteral hypodermic drug delivery applications, all the areas of the device that come in contact with the deliverable substances and the areas that will come in contact with the body of the subject need to be maintained sterile until the time of use. In the arrangement of FIG. 1c, the aseptic engagement of the injector 11 and the cartridge 10 maintains the sterility to that area. The sterility of the inner side of the barrel 13 may be maintained through a second seal at the back end of the body 13, a local overwrap of portions of the back of the body 13 and the piston 14, or a sterile overwrap to the entire device. Similar solutions will apply to the arrangement of FIG. 1b with the addition that aseptic covers would be needed for the front area of the injector body 13 and the fitment 12.

The sterility of the fitment 12 may be achieved with a lead or a cap protecting the port area. A foil lead may be heat-sealed to the circumference of the vertical walls around the port. In one embodiment, the cartridge 10 is stored in a sterile overwrap. In some embodiments, wherein at least one of the substances is in dry format it may be advantageous to include a drying agent such as a desiccant capsule, pellets, or gel in the sterile overwrap, to avoid moisture from migrating to the dry compartment across the web 18, 18' wall. In one embodiment, the drying substance may be integrated in the web (this arrangement is sometime referred to as scavenger film). Packaging the cartridge separate from the injector will improve the controlled-conditions storage and transportation of the drug product. The sterility of the front end of the body 13 in the arrangement of FIG. 1b can be achieved in various ways including a tight cap, a thermally sealed foil around the nozzle 17 area, and by packaging the entire injector in a sterile overwrap. The arrangement of FIG. 1c may therefore be advantageous to reduce the measures that need to be taken to maintain sterility of the product.

Referring now to FIG. 1d, the arrangement of FIG. 1c is shown after the frangible seals (19' and 19" in FIG. 1c) have been ruptured, and a joined compartment 16' is formed in fluid communication with the passageway of fitment 12.

Figure 1E:
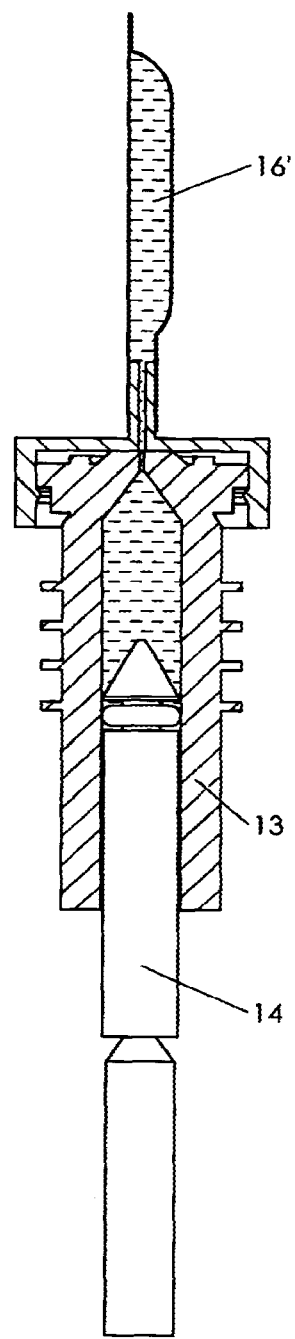

FIG. 1e shows the arrangement of the previous FIG. 1d, when the piston is retracted from the body 12, causing the fluid from the joined compartment 16' to flow into the injector 11.

Figure 1F:
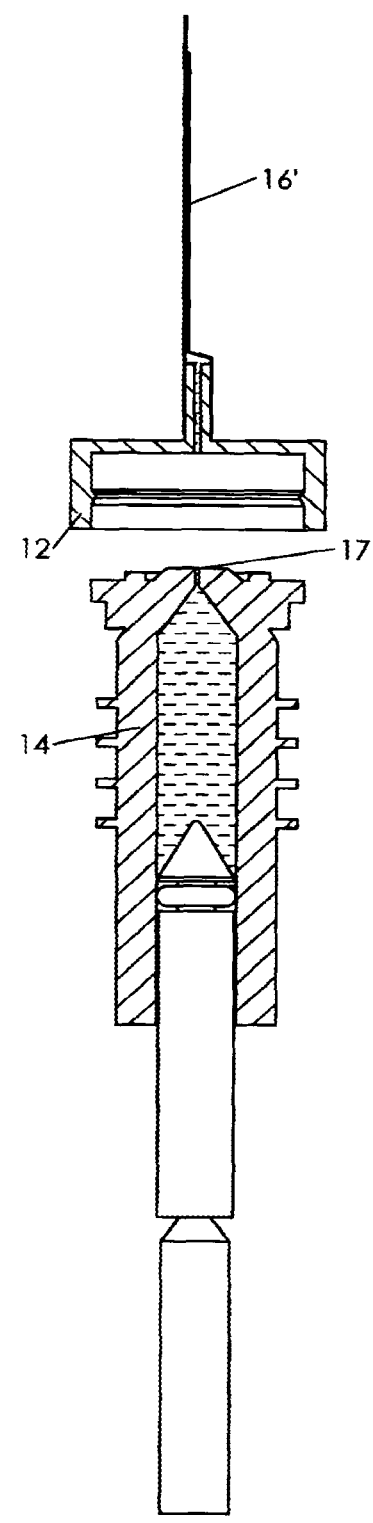

FIG. 1f shows the arrangement of the previous FIG. 1e where the piston 14 is in a fully retracted state. The joined compartment 16' is fully depleted, and its content is fully transferred to the injector 12. The cartridge 11 is removed and the injector 12 is now loaded with the deliverable product dose and is ready to use. Where the arrangement was pre-sterilized, the front portion of the injector was maintained sterile until this point where the fitment 12 is removed. This arrangement may be advantageous compared to commercially available arrangements wherein the injector's application surface is exposed to non-sterile field even before the injector filling step, increasing contamination risk to the subject.

The present arrangement is showing an aseptic filling arrangement of a jet injector cartridge. In further arrangements of the present disclosure, a similar arrangement is provided to fill other cartridges, dispensers, or drug delivery devices known in the art including, for example, intramuscular, subcutaneous, or intradermal injectors, and their cartridges, topical applicators and their cartridges and reservoirs, infusion pumps, micro-infusion pumps, infusers, micro-infusers, patch delivery devices, and their cartridges and reservoirs, infusion containers including infusion bags and infusion bottles, oral, ocular, or ear dispensers and their cartridges and reservoirs, glue dispensers, and other dispensers, delivery device and applicators for various form of use and purpose.

Figures 2A, 2B:
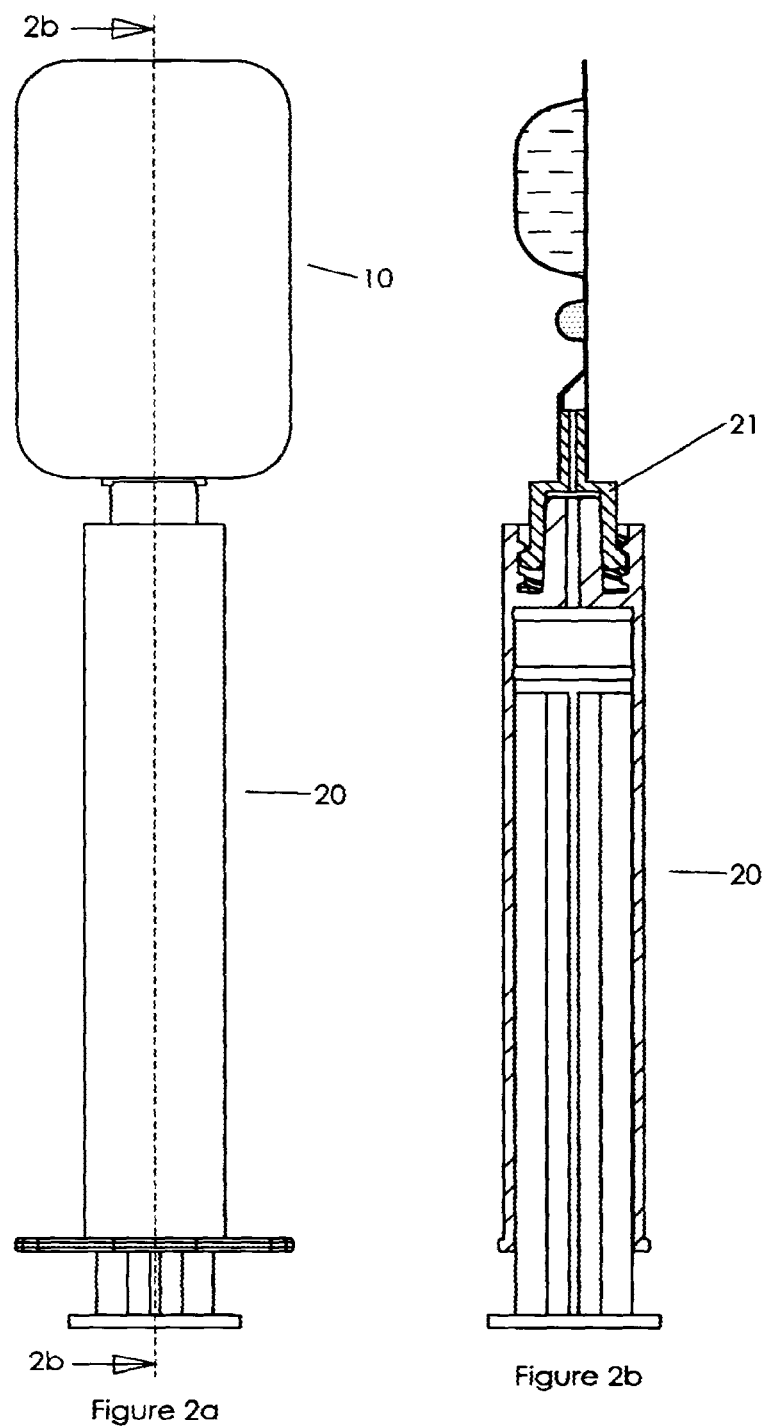
FIGS. 2a and 2b illustrate a syringe assembly with a blister package associated with its cap, which can be employed to various configurations.

FIG. 2 illustrates an arrangement of a prefilled mixing cartridge 10 and a regular syringe 20. The figure provides a section line of the section view of FIG. 2b. Referring to FIG. 2b, the cartridge 10 comprise a fitment terminating with a Luer Lock female connector, coupled with a Luer Lock male connector of the syringe 20, and forming a fluid tight connection between the cartridge 10 and the syringe 20. The fluid may be transferred from the cartridge 10 to the syringe 20 in the same fashion as with the injector of FIG. 1. The Syringe tip will remain in an aseptic environment until the time of use where the cartridge 10 will be removed. This arrangement may be advantageous compared to commercial products where the syringe tip or the tip of a needle are exposed to non sterile field prior to the filling step, which increases the risk of contamination to the subject. In one arrangement, the cartridge is maintained separate from the syringe until the time of use, when they are integrated through the Luer coupling. To maintain the sterility of the syringe 20 and the cartridge 10, similar arrangements and measures may be taken as described above for the arrangement of FIG. 1b.

Referring to FIG. 3, another arrangement is provided wherein the cartridge is associated with the back end of the piston 31. The piston 31 comprises a fluid passage 32 along its axis, communicating the cartridge port 9 and the syringe body. At the front end of the piston 31 a plunger 34 is arranged such that when the piston 31 is retracted, the friction of the plunger 34 with the barrel 33, cause the plunger 34 to slightly displace away from the piston 31, thereby open a fluid path 35 (see arrow) allowing the content of the cartridge to transfer into the barrel 33. A cap 37 maintains an aseptic space around the syringe's dispensing tip 36. FIG. 3b illustrates the arrangement of FIG. 3a after the piston 31 has been retracted to the fully retracted position and is being advanced. The cartridge 10 is completely depleted of its content. The plunger 34 is replaced at the closer position to the piston 31 head thereby sealing the passageway 32, such that the content of the barrel 33 can only advance to the syringe port 36 when the piston 31 is advanced.

Unlike commercial syringes where the dispensing tip or a needle associated with it, are exposed to non sterile field prior to the filling process, in the current configuration the cap is removed from tip 36 just prior to use, and only after the filling process. The cartridge may be coupled with the syringe by various means known in the art including, for example, Luer connector, barb connector, press fit connector, a septum arrangement, a coupling tube, or adhered to each other. In one arrangement, the cartridge is disposed inside a hollow space in the piston.

Referring now to FIG. 4, an arrangement is illustrated where the cartridge 10 is connected to the back end of the piston 43, and extending in a lateral direction from piston 43. A valve 44 is disposed at the back end of the fluid passageway 42 allowing fluid to transfer from the cartridge 10 to the barrel 40, but prevents fluid from flowing in the opposite direction, thus causing the entire dose to flow only to the dispensing tip 45 when the piston is advanced. In one arrangement the piston 44 also allows air into the flow passageway 42 after the cartridge 10 is emptied thus advancing the fluid from the passageway to the barrel. In one embodiment, a dedicated aseptic compartment allows air of water into the fluid passageway 42 after the beneficial agent the cartridge is emptied from the beneficial agent, to wash the passageway from the residual beneficial agent. In one arrangement said water or air compartment is part of the cartridge 10 assembly.

Figure 5A:
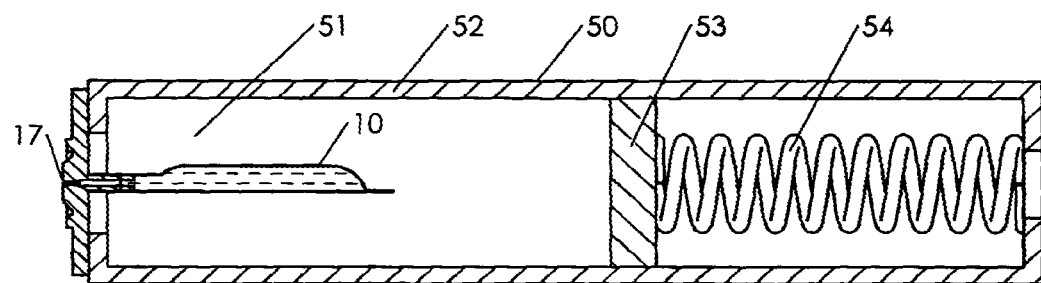
FIGS. 5a and 5b illustrate a prefilled cartridge in a spring powered needle-free auto injector.

FIG. 5a illustrates a jet injector comprising a cartridge 10 disposed in a pressure chamber 51 in the injector body 52. The cartridge 10 comprises a needle-free jet nozzle 17 associated with the front end of the injector body. A piston 53 is disposed in the body 52 and is detained in its peruse position by detaining mechanism (not shown), and is biased forward to deplete the volume of the pressure chamber 51. In one arrangement, the cartridge 10 comprise more than one compartment prior to use, and those are manually mixed by removing the cartridge 10 and following a similar procedure as described in FIG. 1; then replacing the cartridge 10 in the body 52.

Figure 5B:
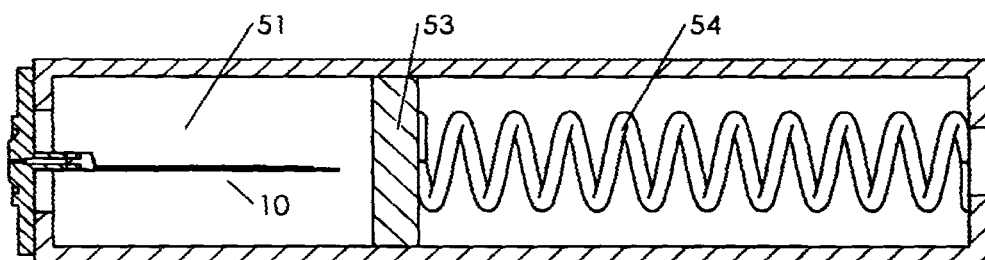

FIG. 5b shows the injector 50 after the piston 53 has been released from the detent mechanism and has been forced forward by spring 54 and pressurized the pressure chamber 51, thereby causing the cartridge walls to collapse and express the content of the cartridge 10 through nozzle 17. The nozzle 17 may be protected by an aseptic cap or adhered foil until the time of use.

Figure 6:
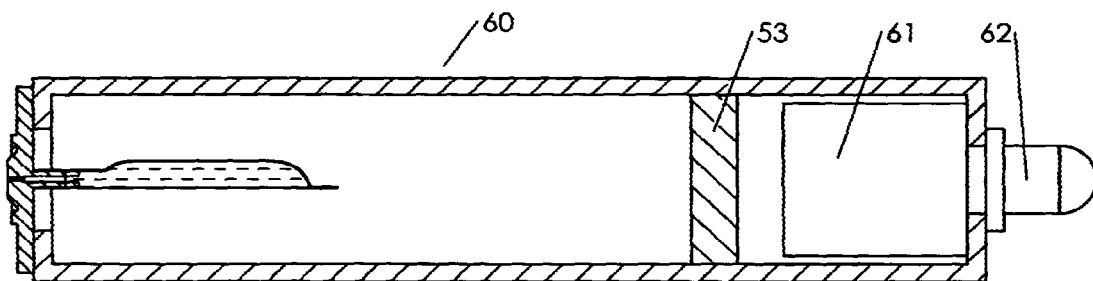
FIG. 6 illustrates a prefilled cartridge in a pyrotechnically powered needle-free auto injector

FIG. 6 shows a similar arrangement to that of FIG. 5 with the exception that the piston is biased forward by pressurized gas, generated by a pyrotechnic module 61 when the last is activated by manual switch 62.

Figure 7:
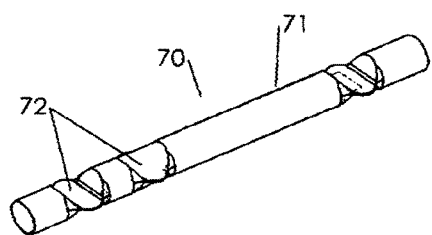
FIG. 7 illustrates a cartridge made from an extruded tube.

FIG. 7 shows a cartridge 70 made from a tube section 71 that is pinched and heat sealed 72 across the tube section 71 in a number of locations 72 along the tube section 71 to form at least one compartment comprising a beneficial agent. In one configuration of the cartridge 70 the seals at the pinching locations 72 are frangible seals made such that they will peel apart under the presence of threshold pressure or force. The tube section 71 may be made by extrusion, injection molding, blow molding or other manufacturing methods known in the art. In one arrangement, the tube section 71 comprises a number of layers where the inner layer is a heat sealing material and at least a second layer provides improved barrier properties to reduce transfer of certain gasses or moisture across the tube wall. In one arrangement, the tube is co-extruded. In one arrangement, at least one first layer of the tube wall is made from a rolled sheet of plastic, metal, or metal oxide, and at least one second layer is extruded over said rolled first layer.

Figure 8:
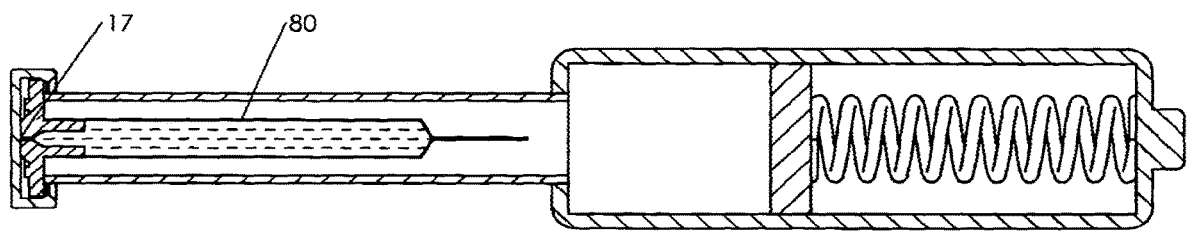
FIG. 8 illustrates a cartridge made from extruded tube, loaded in a needle-free auto-injector.

FIG. 8 shows a needle free jet injector arrangement similar to the arrangement presented in FIG. 5, with the exception that the cartridge 80 is made from a tube section, to which a jet nozzle 17 is attached to its front end.

Figure 9A:
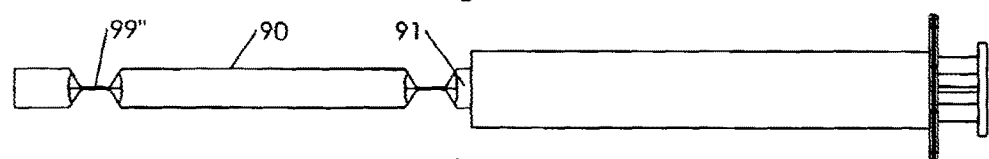
FIG. 9a illustrates a cartridge made from extruded tube, mounted onto a syringe.
Figure 9B:
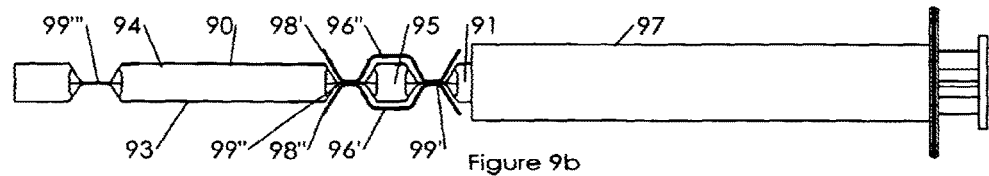
FIG. 9b illustrates a cartridge made from extruded tube comprising a peelable protective foil, mounted on a syringe

FIG. 9a shows a syringe and cartridge assembly similar to the arrangement presented in FIG. 3, with the exception that the cartridge 90 is made from a tube section 90 in pinched and sealed across in two points 99' and 99'" to form a compartment. Seal 99' is a frangible seal that would rupture when the cartridge is compressed and the content is pressurized, to allow fluid communication between the syringe and the cartridge to which a female Luer Lock connector 92 is attached at its end. The tube section in some arrangements the cartridge 90 may be maintained separate from the syringe until the time of use. Sterility of the product and the device may be accomplished in similar fashion and measures as described in FIGS. 1 to 3 above. The tube wall may incorporate a single layer or multi layers and may incorporate a high barrier PCTFE layer, an aluminum layer, a COC layer, and a peelable adhesive layer FIG. 9b shows a further arrangement where of a cartridge made from tube where a first seal 99' and a second seal 99" define a first compartment 95, and the second seal 99", holding a first substance, and a third seal 99'" define a second compartment 94 holding a second substance. The second seal 99" is rupturable upon pressurizing either or both of the first compartment 95 and the second compartment 94; to allow the first substance and the second substance to merge.

The first seal is rupturable to establish fluid communication between the cartridge and a syringe 97. The cartridge further comprises peelable barrier shells 96' and 96" sealed to each other and across the first and second pinched seal sections 99' and 99"; enhancing the barrier between the cartridge surrounding and the first compartment 95. This arrangement may be particularly advantageous where the barrier properties of the tube 93 are insufficient to protect the first compartment 95 from moisture, oxygen or light transmission.

The tube material may preferably be transparent to allow visual inspection of the contents, which generally compromise some of the barrier properties. The peelable shells may include a high barrier aluminum layer that prevent visual inspection of the cartridge contents, and hence the need to peel the shells for inspection. A first tab 98' and a second tab 98" are provided as extensions to the first and second peelable shells 96' and 96", respectively, to facilitate the peeling of the shells with the fingers. The peelable shells may be pre-formed to accommodate the shape of the first compartment 95. At least one of the peelable shells 96' and 96" may be extended to form a barrier shell to the second compartment 94. At least one of the peelable shells may be extended to provide a printable, or otherwise markable, surface, including graphics, text, barcode or other optical machine-readable representation of data, which shows data about the content of the cartridge, operation instructions, warnings, etc. The peelable shells may be made from a single or multi-layer film or foil (together "web") and may include a pressure sensitive adhesive, electrostatic adhesive or temperature sensitive adhesive to form the peelable seal.

Figure 10A:
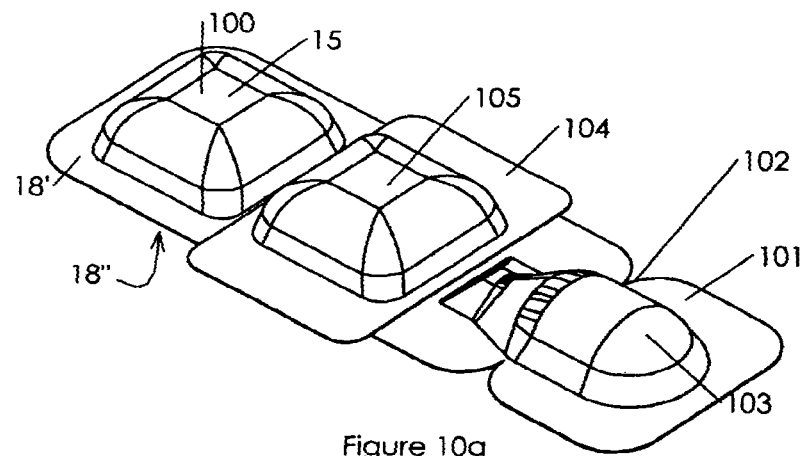
FIGS. 10a to 10e illustrate a cartridge with a peelable portion of the formed-wall and a an extended walls portion forming an aseptic compartment around the dispensing port, and a number of operation steps.

FIG. 10a shows another preferred arrangement 100 in which the second compartment 16 comprises a peelable layer 105. For various applications it is desired to have at least a portion of the package made from a clear material, for instance, in application where it is desired to visually (or by optical instrumentation) inspect the content of one or more compartments, or the merged compartment after combining the content of two or more compartments. However typically clear materials have higher moisture vapor transmission rate (MVTR) than foils, which are opaque, providing lower barrier between the compartment(s) and the surrounding of the package. Some products are extremely sensitive to moisture such as dried vaccine with which potency may be compromised with relative humidity levels higher than 2% or 3%. Yet visual inspection of the vaccine powder is important prior to use to ensure that the product has not been tampered; and after mixing, to inspect complete dissolution of the vaccine powder with the diluent.

In one arrangement of this disclosure the cartridge is stored in a desiccant containing overwrap, keeping dry environment around the cartridge. In one arrangement, the overwrap material is of the type known in the industry as "scavenger film" in which a desiccant substance is embedded in the composition of the web material. In FIG. 10a the powder compartment of the package 100 comprises a peelable high-barrier formed layer 104, which is opaque, or has limited optical transparency. In some arrangements, the peelable layer may provide a barrier from light. High barrier clear materials are typically more costly than low barrier clear materials. In some arrangements, the localized, peelable layer 104 is made from high barrier clear material such as a film containing an Aclar (Honeywell), while the larger, formed-wall of the package 18' is made from a low barrier material to reduce manufacturing costs. The peelable layer 104 may provide other desired properties that the formed-wall 18' lacks. The peelable layer 104 may be part of the composition of the raw material that the formed-wall 18' is made of. The peelable layer 104 may be made from a separate web of the first wall 18', and in one manufacturing arrangement, the two webs are formed together. In some arrangements, where the wall 108' is a thermoformable film, and the peelable layer 104 is a cold-formed foil, the forming process may involve a step combining cold forming and thermoforming.

In some arrangements, the cavity 105 in the peelable layer 104 is formed separate from the formed-wall 18' and is subsequently attached to the package in a sealed fashion. Attaching the peelable layer 104 to the package may be achieved by one of the means known in the art including an adhesive, a glue, pressure sensitive adhesive, heat stake welding, ultrasonic welding, etc. In one arrangement, the peelable layer 104 is sealed to the first wall 18' via a die-cut adhesive sheet. The die-cut adhesive may be adhered to the first wall 18', and at a subsequent stage the peelable layer 104 is attached to it. Alternatively, the die-cut adhesive may be adhered to the peelable layer 104, and at a subsequent stage the first wall 18' is placed attached to it. The peelable layer 104 may comprise an aluminum lamination or aluminum coating.

Figure 10B:
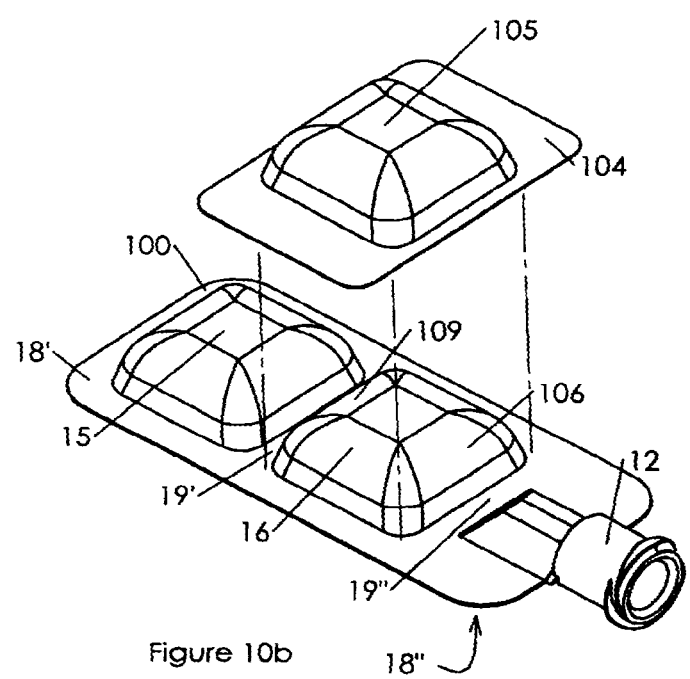

The arrangement 100 further comprises a dispensing port compartment 103 maintaining the dispensing port in an aseptic enclosure until the time of use. The dispensing port compartment 103 is formed in an extension 101 of the web materials of the package 100. A tear-off notch 102 provides for an easy removal of extended portion 101 exposing the dispensing port. FIG. 10b shows the arrangement 100 after the peelable layer 104 has been removed, allowing for visual inspection of the content of the second compartment through the clear wall 18'. In addition, extension 101 has been removed, exposing a dispensing port 12 in the form of a female Luer Lock connector. In some procedures it will be desired to merge compartments 15 and 16 prior to removing extension 101 to minimize the exposure of the dispensing port and reduce the risk of contamination. The second wall 18" of the package 100 is preferably made from high barrier material such as a laminated aluminum foil, SiOx laminate, AlOx laminate or other materials known in the art.

In some arrangements the second compartment 16 is depressed to rupture the first barrier 19' between the first compartment 15 and the second compartment 16, to cause the two compartments to merge; and to rupture the second barrier 19" between the second compartment 16 (or the merged compartment (15+16). The pre-formed structure of the second compartment 16 allows controlling the rupture of each of barriers 19' and 19" at a desired sequence and timing. The deep form of compartment 16 provides that when the compartment 16 is depressed at its distal end 106, the strain in this area 106 of the first wall 18', and the seal of the first wall 18' and the second wall 18" proximal to this area 106 is relaxed; while the proximal area 109 of the first wall 18' opposite to the depression zone 106, and the seal between the first wall 18' and the second wall 18" proximal to that proximal area 109 is strained; resulting in rupture of the first barrier 19', while the second barrier 19" remains intact.

At a subsequent step, the merged compartment (not shown) is pressed at its proximal area to excess the strain on second frangible seal 19" causing it to rupture and establish fluid communication between the merged compartment and the dispensing port. In addition to, or as an alternative to the aseptic dispensing port compartment 103, the port may be aseptically sealed with a plug (such as a male Luer Lock cap), a welded foil portion, a stopper (such as a rubber stopper, or by any other means known in the art. The second frangible seal may be avoided if other sealing features are aseptically protecting the content and preventing it from spilling.

Figure 10C:
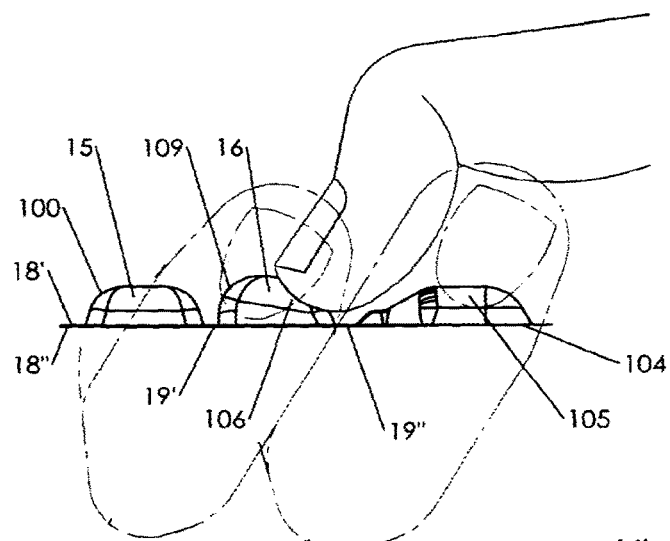
Figure 10D:
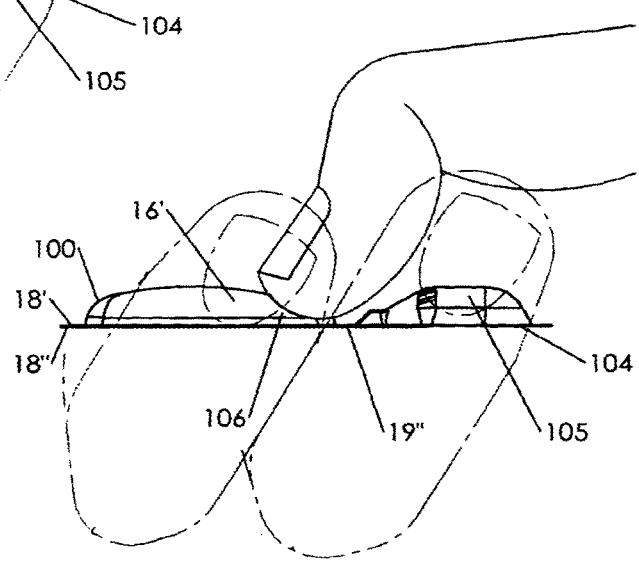
Figure 10E:
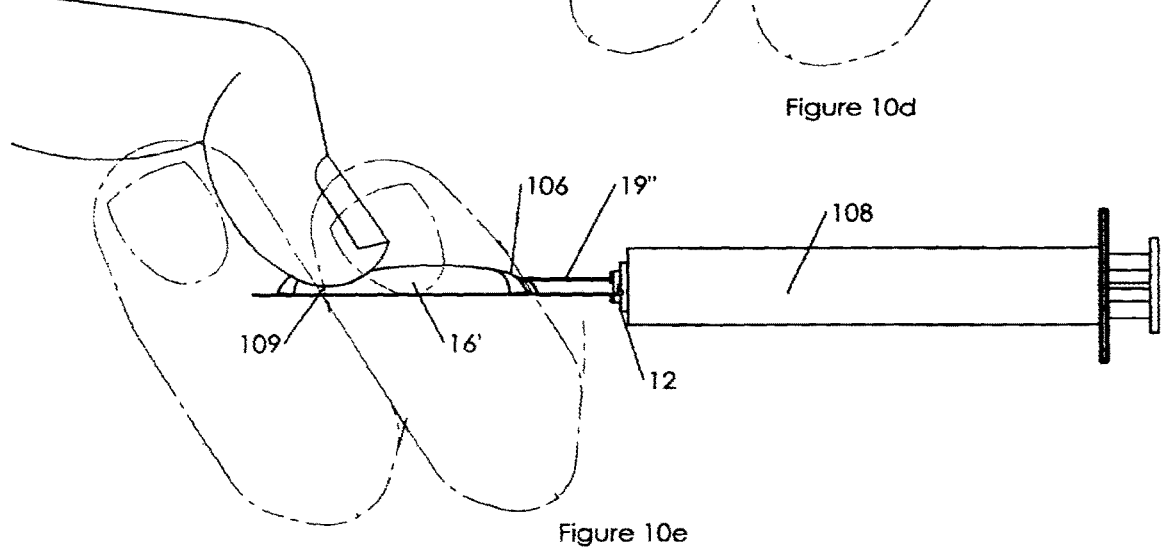

FIG. 10c to FIG. 10e show one way of operating the cartridge 100 to achieve a controlled and sequenced rupture of the frangible seals 19' and 19" by direct operation of the thumb of the operator. The cartridge 100 is resting in the palm of the operator on the index finger and the middle finger. In FIG. 10c the second compartment 16 is depressed by thumb on its distal portion 106. As a result the wall 18' at the proximal area 107 of the first compartment 16 is strained exerting peeling force to the first frangible section 19'. At the same time the depression of the thumb on the distal area 106 of the second compartment 16 prevent strains from that area of the first wall 18', thus the peeling force on the second frangible section 19" is eliminated or minimized. As a consequence, shown in FIG. 10d, the first compartment and the second compartment become merged compartment 16' while the second frangible seal 19" remains intact, allowing the substances of the two compartment to mix prior to communicating the dispensable product with the dispensing port. The configuration of FIG. 10d allows putting the cartridge aside, for example in order to let the substances to mix properly, without exposing to contamination risks, as the dispensing port is still sealed in the dispensing port compartment 104, and the merged compartment 16' is still not in communication with the dispensing port.

In FIG. 10e the dispensing port compartment has been tore off and the port 12 is engaged with a syringe 108. The merged compartment 16' is depressed with the thumb at its proximal end 107 causing the wall at the distal end 106 of the merged compartment to strain and exert peeling force on the second frangible seal 19", causing it to rupture and establish fluid communication between the syringe 108 and the merged compartment 16' via the dispensing port 12. In other arrangements, the depression of the compartments is done by a compressing object such as a flat panel or a roller. This disclosure advantageously teaches a drug cartridge for filling an injector where the fluid communication between the cartridge and the injector is established only after the injector and the cartridge have been secured in a sealed tight fashion, limiting the exposure of the injectable product to non-sterile field, and reducing the risk of the product spillage. Typically with vials and ampoules the fluid communication is established during the integration of the injector and the cartridge, typically by a spike penetrating a septum seal.

Figure 11:
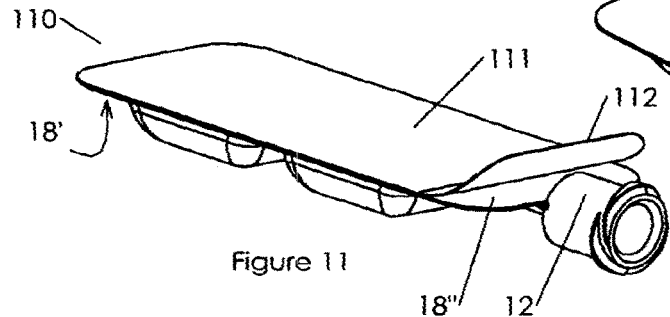
FIG. 11 illustrates a cartridge with a peelable portion of the flat wall.

FIG. 11 shows an arrangement where the second wall 18" of the package comprises a peelable layer 111, providing enhanced moisture barrier to the substances in the compartments. The formed-wall 18' is preferably made from a cold formed aluminum laminate providing a high barrier to moisture and gasses. A tab 112 provides an easier peel of the second wall 18". In some arrangements, the peelable layer 111 is attached to the second wall 18" by one of the means known in the art such as welding or adhesion. In one arrangement, the peelable layer 111 is a label with a pressure sensitive adhesive. In some arrangements, the pressure sensitive adhesive is selectively disposed on the label such that certain areas of the label are free from the pressure sensitive adhesive.

The peelable layer preferably comprises an aluminum layer providing a high barrier to moisture and gasses until it is being peeled off. In some arrangements, the peelable layer is part of the multi-layer material composition of the web that makes the second wall 18". In some arrangements, the peelable layer is removed from the entire second wall 18".

In some arrangements, a scored or die-cut pattern defines the area of the peelable layer 111 that will be removed. In some arrangements, a scored section of the first wall 18' and the second wall 18" is scored or die-cut, providing a tab, or a break-off tab that facilitates the removal of the peelable layer 111. The cartridge 110 may be readily attached to an injector, a drug delivery device, a reservoir of these or other systems, or it may comprise a closure that is removed prior to use. The peelable layer 11 may include printed (or otherwise marked) information and may be attached to a person, a device, the drug delivery device receiving the content of the cartridge 110 (such as a syringe), or a document after it has been peeled off from the cartridge 110, as a label presenting that information.

It is understood that other labels may be attached to the cartridge arrangements according to this disclosure, said labels may include printed or otherwise marked information; and may be non-peelable or peelable and further attached to other objects such as a person, a device, or a document. In some arrangements, an information containing portion of the cartridge may be tearable or otherwise detachable from the rest of the cartridge in order to include or present this information else where such as on a document, attached to a patient, or to a device.

Figure 12:
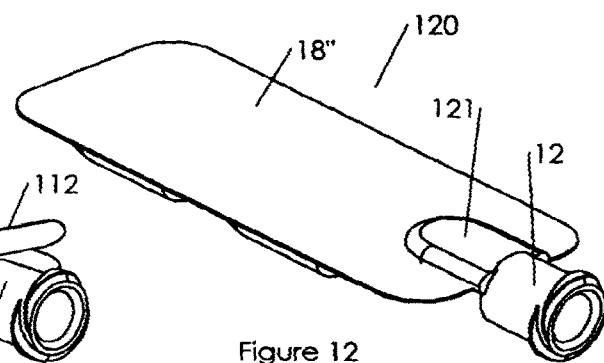
FIG. 12 illustrates a cartridge with a flanged dispensing port attached to the external side of the wall of the cartridge.

FIG. 12 shows an arrangement where the dispensing port is attached to the external side of the second wall 18" via a flange 121. The flange comprises a conduit (not shown) aligned with an opening in the wall 18" (not shown) which communicates the content of the package with the dispensing port. The port 12 is attached to the wall 18" by one of the means known in the art including heat welding or adhesion. The cartridge 120 may be readily attached to an injector, a drug delivery device, a reservoir of these or other systems; or it may comprise a closure that is removed prior to use.

Figure 13:
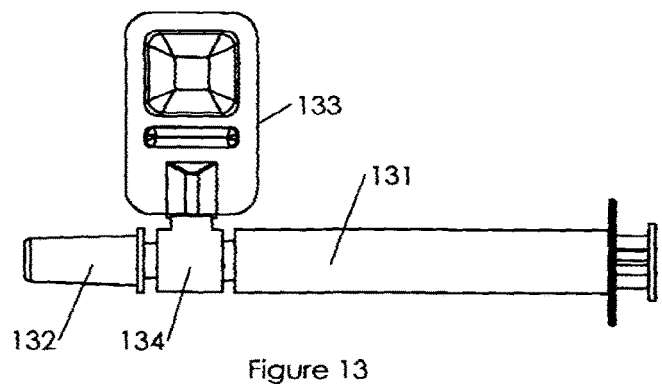
FIG. 13 illustrates a cartridge associated with a valved-coupler communicating to a syringe and a needle.

FIG. 13 shows an arrangement where the cartridge 133 is associated with a manifold 134 disposed between a syringe 131 and a needle (shown here covered by a needle shield 132). The manifold comprises a valve arrangement which, after the cartridge 133 has been activated, draws the content of the cartridge 133 into the syringe 131 when the syringe's piston is retracted; and delivers the content of the syringe 131 to the needle when the piston is forwarded. In some arrangement a manipulation of the manifold will cause disengagement of the cartridge from the manifold 134 when shifting from a dose drawing configuration to a dose injection configuration. U.S. Pat. No. 7,879,018 teaches a number of manifold arrangements for accomplishing the same and is incorporated herein in its entirety by this reference.

The arrangement of this FIG. 13 discloses a unique arrangement of a prefilled syringe where the piston is in an inward position prior to use, advantageously affecting the product's packaging efficiency. A needle safety feature and a syringe disabling feature may be incorporated with this arrangement. US Pat. Publication No. 2009/0221962 teaches a retractable syringe and plunger. The syringe has a barrel, a retractable needle mount to which is mounted or is mountable a needle, and a plunger, the plunger comprising an initially compressed spring, a means for engaging the retractable needle mount, an integrally formed plunger seal and a removable controlling means for facilitating control of the rate of retraction of needle mount when engaged with plunger. The needle mount is held in the barrel by a holding means which prevents inadvertent retraction of the needle mount when the plunger is withdrawn to fill the syringe. The holding means comprises a plurality of clips that may be integrally formed with the barrel or may be present on a cap mounted to the barrel. An ejector means is also provided, whereby plunger depression can urge the ejector means to release the needle from the holding means and thereby allow retraction of the needle mount following decompression of the spring. In one arrangement of the present disclosure the cartridge is associated with a syringe with a retractable needle mount such as the one taught by US Pat. Publication No. 2009/0221962.

Figure 14:
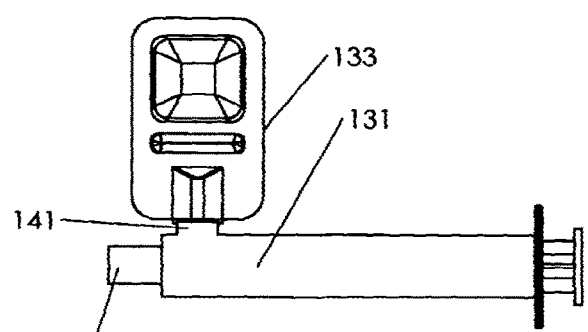
FIG. 14 illustrates a cartridge associated with the distal end of a syringe barrel.

FIG. 14 shows a cartridge 133 comprising a valved port 141, connected with a syringe 131. For the step of loading the syringe barrel with the dispensable product from the cartridge 133, the Luer cap 142 is maintained in place. After merging the compartments of the cartridge 131 and popping the barrier between the merged compartment and the dispensing port 141, the valved port 141 provides that when the syringe's piston is retracted, the dispensable product will flow from the cartridge 133 to the syringe barrel, and when the piston is advanced, the dispensable product is urged to the syringe tip, and will not return to the cartridge. In one arrangement, the valved port comprises a check valve allowing fluid to flow out of the cartridge 133, and prevent reversed flow into the cartridge 133. In one arrangement, the valved port is manually operated, for instance by rotation, axial movement, or a combination of these, to switch between an open state to a closed state.

In some arrangements, the cartridge is removable either during the manual operation or post that. U.S. Pat. No. 7,879,018 teaches a number of manifold arrangements for accomplishing the same and is incorporated herein in its entirety by this reference. In some arrangements, the syringe 131 is valved such that no flow is allowed through the syringe's tip when the syringe's piston is retracted, and flow is allowed to flow out of the syringe's barrel when the piston is advanced. In some arrangements, said syringe's valve is a check valve. In some arrangements, the syringe's valve is manually operated. In some arrangements, the syringe's valve and the cartridge's valved port 142 are mechanically linked such that the operating the cartridge valved port 142 to shutoff, operates the syringe's valve to open, or vise versa. The arrangement of FIG. 14 may be particularly advantageous where the dispensing tip is in a fashion that can not accept a cartridge, for instance where the dispensing tip incorporates a staked needle, a retractable needle, or other safety mechanisms.

US Pat. Publication No. 2011/0015572 teaches a retractable syringe, plunger and releasable needle retaining assembly. The retractable syringe typically has a glass barrel and is prefilled with fluid contents before use. The releasable needle retaining system comprises a retractable needle, a needle seal, a retaining member and an ejector member that is operable to release the retractable needle from the retaining member. The retaining member has a mating surface for mounting to a complementary mating surface of an interior wall of a syringe barrel. The plunger comprises a plunger outer, a plunger rod frangibly connected to a controlling member, a spring and a unitary plunger seal capable of engaging the retractable needle, wherein the plunger rod, plunger outer and the controlling member co-operate to releasably maintain the spring in an initially compressed state. After delivery of fluid contents of the syringe, the plunger forces the ejector member to release the retractable needle from the retaining member. Decompression of the spring at the end of depression of the plunger facilitates retraction of the retractable needle when engaged with the unitary plunger seal. Dual locking systems prevent reuse of the syringe after needle retraction. In one arrangement of the present disclosure, the cartridge 133 is associated with the barrel of a safety syringe such as the one taught be US Pat. Publication No. 2011/0015572, via a valved port 141 arrangement of FIG. 14.

Figure 15:
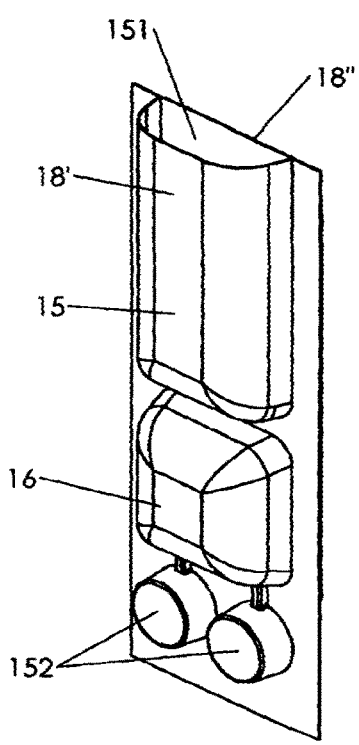
FIG. 15 illustrates a semi-finished cartridge ready for lyophilization of a beneficial agent.

Referring now to FIG. 15, in some arrangements it is desired to lyophilize (freeze dry) a substance directly in compartment 15. The first wall 18' is pre-formed and welded to the flat, second wall 18". The first compartment 15 is open ended and longer than the final, sealed dimensions of this compartment. The compartment allows 15 enough for filling a liquid substance. The cartridge is then placed in a freeze drier until the lyophilization process is completed, leaving a dry cake at the bottom of the first compartment 15. The compartment is then sealed to aseptically contain the lyophilized dose. The second compartment 16 may be filled and sealed prior to the lyophilization process or after it.

Figure 16:
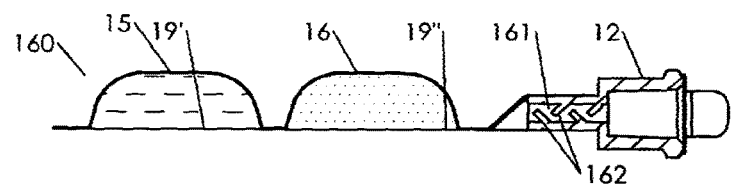
FIG. 16 illustrates a cartridge comprising a static mixer at its dispensing port facilitating the mixture of two constituents stored in the cartridge.

Referring to FIG. 16, a further arrangement of a cartridge 160 is shown comprising a first 15 holding a first substance, and a second compartment 16 holding a second substance; the compartments are separated by a frangible seal 19' that is rupturable to allow the first substance and the second substance to merge. The second compartment 16 is separated from a female Luer Lock fitment 12 by a second frangible seal 19" that is rupturable to allow fluid communication between the cartridge and a dispensing device such as a syringe or an injector. The fitment 12 comprises a fluid passageway 161, and a static mixer 162 disposed in said fluid passageway 161. The arrangement is such that when the merged first substance and second substance are transferred from cartridge 160 to a dispensing device the static mixer enhances the mixing of these substances to form a more homogeneousness product. An example of a static mixer is taught in U.S. Pat. No. 4,538,920 incorporated herein in its entirety by this reference. The mixture may further be transferred back and forth between the delivery device and the cartridge to repeat the mixing action at the static mixer. In some arrangements, the static mixer is constructed as a pattern of passageways formed between the walls of the flexible package by welding and pre-forming designated areas of the walls. The static mixer may be merely a narrow nozzle, or a porous component accommodated in the flow passageway between the cartridge and the delivery device.

Figure 17:
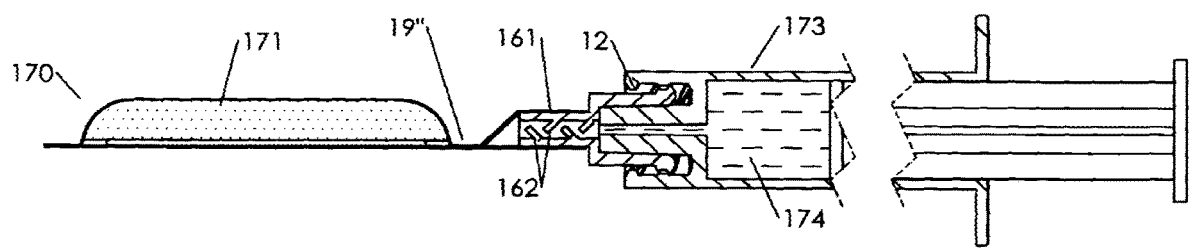
FIG. 17 illustrates a system for mixing a first constituent contained in a cartridge and a second constituent contained in a syringe.

FIG. 17 shows a preferred embodiment in which the cartridge 170 comprises a compartment 171, containing a first substance, and separated from a female Luer Lock fitment 12 by a frangible seal 19". The fitment comprises a fluid passageway 161 and a static mixer 162 disposed in said fluid passageway 161. A syringe 173 containing a second substance 174 is attached to the cartridge 170. The frangible seal 19" is rupturable to allow the first substance and the second substance to merge. By drawing the syringe piston the first substance is drawn out of the compartment 171 into the syringe and merges with the second substance in the syringe. The syringes piston may be operated back and forth to transfer at least a portion of the mixture into and from the cartridge 170, and create a more homogenous mixture as the material flows through the static mixer 162. In one arrangement, the compartment 171 is sufficiently expandable to receive the total volume of the first substance and the second substance. In some arrangements, the cartridge 171 may comprise more than one compartment that may be merged with the first compartment 171 before or after merging the first compartment with the syringe. It will be obvious to those skilled in the art that a static mixture may be implemented in any of the previous arrangements of this disclosure in similar arrangements to that of FIG. 16 or FIG. 17.

In particular, referring back to FIGS. 3 and 4, the static mixer may be disposed in the syringe's stem or plunger.

Figure 18:
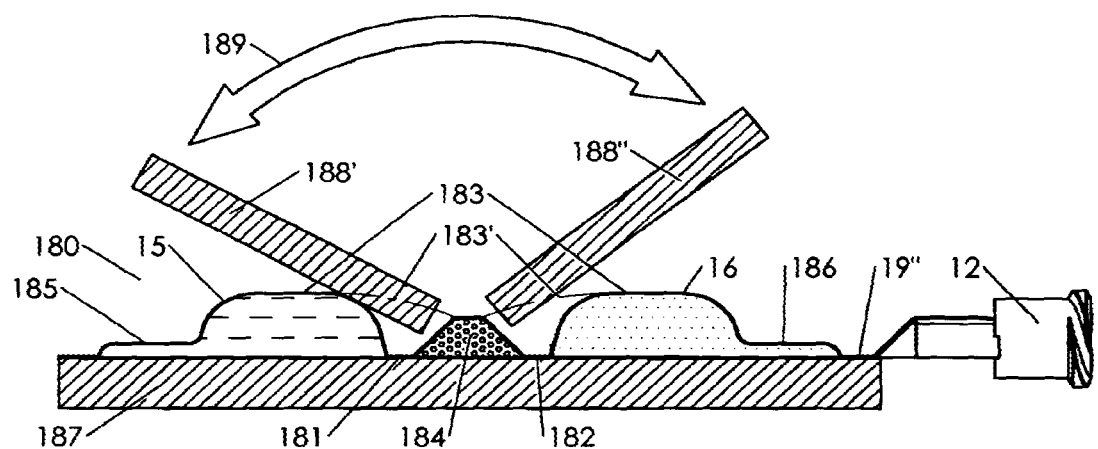
FIG. 18 illustrates a system for mixing a first constituent and a second constituent contained in a cartridge.

FIG. 18 shows another arrangement of a cartridge 180, comprising a first compartment 15, containing a first substance; a second compartment 16 containing a second substance; a static mixer 184, disposed between the first compartment 15 and the second compartment 16, and separated from the first compartment 15 by a frangible seal 181, and from the second compartment 16 by a frangible seal 182. At the point that the first substance and the second substance are to be mixed, the first frangible seal 181 and the second frangible seal 182 are ruptured such that the upper wall 183 is rearranged as indicated by dashed line 183' to allow the first substance and the second substance to communicate via the static mixer 184. The first compartment 15 and the second compartment 16 are not fully inflated as the first recessed area 185 of the first compartment 15, and the recessed area 186 of the second compartment can expand to receive substance from the other compartment; hence a good mixture of the first substance and the second substance may be achieved by alternately compressing the first compartment 15 and the second compartment 16, and transferring the mixture of the first and second substances through the static mixer 184. The static mixer 184 is shown here as a porous body, and alternatively be other static mixer known in the art.

A third frangible seal 19" is rupturable to establish communication between the mixture and the fitment 12. The arrangement further comprise a backing 187, supporting the cartridge 180; and a rocker, comprising a first compression panel 188' and a second compression panel 188", movable to rotate relative to the backing 187, to alternately depress the first compartment 15 with the first panel 188', and the second compartment 16 with compression panel 188". The rocker and backing arrangement facilitate an efficient operation of the mixture process by more efficiently and systematically compressing the compartments 15 and 16 and transferring the content across the static mixture 184. At the point that the mixture is ready to transfer to a dispensing device through the fitment 12, the first compression panel 188' may be resting where the first compartment 15 is depleted, thus substantially all of the mixture is expressed from the second compartment 16 to the fitment 12. The rocker may be associated with the backing 187 via a hinge or a living hinge, and it may be operated manually or by a device.

Figure 19:
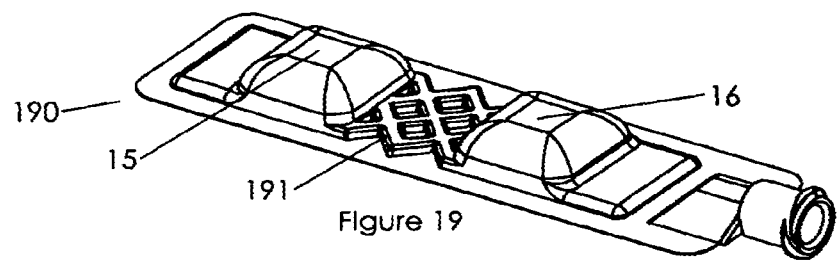
FIG. 19 illustrates a static mixer integrally formed in a blister type cartridge.

FIG. 19 shows another arrangement of a cartridge 190 comprising a first compartment 15, containing a first substance; a second compartment 16, containing a second substance; and an array of pre-formed intercrossing channels there between, providing a static mixer, to enhance the mixing of the first and second substances as they are transported back and forth between the first compartment 15 and the second compartment 16.

Figure 20A:
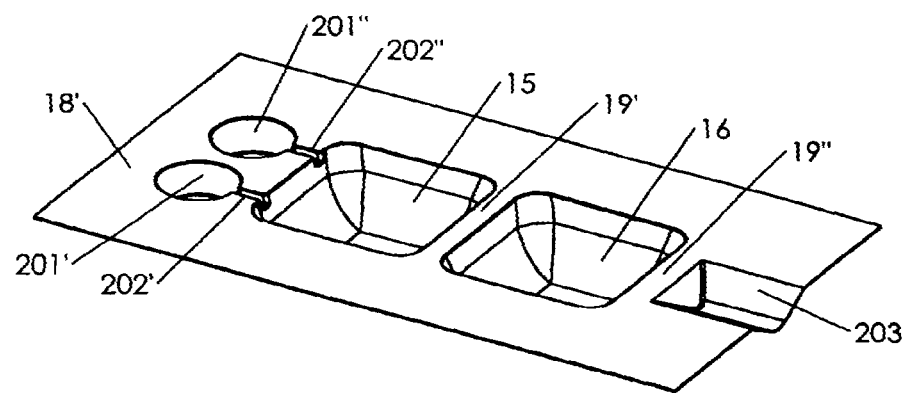
FIGS. 20a to 20e illustrate a method for fabrication the cartridge.

Referring now to FIG. 20a to 20e, one possible manufacturing process of the cartridge is described. In one arrangement, this manufacturing process is accomplished on a Form-Fill-seal system FIG. 20a shows a pre-formed flexible wall 18' of a package for storing constituents of a beneficial agent, comprising a first cavity 15, for receiving a first constituent; a second cavity 16, for receiving a second constituent; and a first uninterrupted area 19' there between; a fitment cavity for receiving a fitment; and a second uninterrupted area 19" between said second compartment 16 and said fitment cavity 203. The first compartment is made to receive a non-fluidic material or a poorly flowing material such as powder, compressed or agglomerated powder, granules, pellets, solid, tablet, capsule, slurry, paste, high viscous fluid, emulsion, and a combination of the above. The first substance is filled to the first compartment by an appropriate filling system to the type of material that needs to be filled. The second compartment 16 may also be filled with water or other low viscosity fluids however it may be challenging to fully fill cavity 16 as surface tension and other properties of the fluid may result in spillage.

Another challenge is that liquid filling is a relatively slow manufacturing process for a number of factors, one of which is avoiding foaming or bubble formation as the liquid is filling the cavity 16. In one arrangement, this challenge is addressed by freezing aliquots of fluid in a mold preferably having the second compartment 16 shape, then handling those as solids into the cavity by one of the means known in the art. The filling system is designed such that heat transfer to the frozen liquid aliquots is limited such that it stays substantially solid until the second cavity 16 is sealed; thereafter the frozen liquid may be thawed. Heat transfer to the frozen aliquots during the filling process may be limited by controlling the temperature throughout this process substantially low; and by selecting contact material to the package with an appropriate heat transfer coefficient. The frozen liquid aliquot may be inspected for weight and other properties and parameters prior to introduction to the second cavity 16.

In one arrangement, more than one frozen aliquots is filled to the second compartment 16, which may have the same, similar or different compositions. These aliquots may have complementary shape that may jointly form substantially the shape of the second compartment 16. In one arrangement, the aliquot is frozen directly in the cavity 16 or on the reciprocal flat wall 18" (not shown) of the package. In another arrangement, the second substance is a loose powder or other form of dispersible dry substance which may be challenging for substantially complete fill of the second compartment 16. Loose powder filling may also be a limiting factor of the manufacturing speed and a challenge for proper inspection of the aliquot fill dose. In one arrangement, in order to facilitate the powder filling, the powder is slightly compressed to form a loosely aggregated tablet, or a unitary body, and is filled in that form into the compartment of the package, by one of the tablet filling means known in the art. A dedicated formulation may be required to achieve the level of aggregation at a given compression rate. The tablet may be inspected prior or during the fill process of the second compartment 16.

In one arrangement, after the tablet has been sealed in the compartment, the compartment is externally manipulated to de agglomerate the tablet, thus improving the substance solubility (or dispersability) at the time of mixing with a dilutent. The external manipulation may include directing energy to the unitary body through the wall of the package via at least one of, but not limited to, compression of the compartment; vibration including, ultrasonic vibration, radio frequency vibration, acoustic vibration; applying mechanical impact to the compartment; and exposure to high or low temperatures. In one arrangement, the unitary body is formed directly in the cavity 16 or on the reciprocal flat wall 18" (not shown) of the package. The first compartment 15 provides another arrangement for efficiently filling a low viscosity fluid to substantially fill the cavity 15. A first filling well 201' and a second filling well 201", are pre-formed in the first wall 18'; and the first pre-formed filling channel 202', and second pre-formed filling channel 202" are connecting them to the first compartment 15. FIG. 20a shows a portion of a web formed to include the details of one cartridge. It would be understood to those skilled in the art that in a normal manufacturing practice an array of details for multiple cartridges may be formed on a larger spread of the first web 18'; and may be handled simultaneously at subsequent forming and filling steps.

Figure 20B:
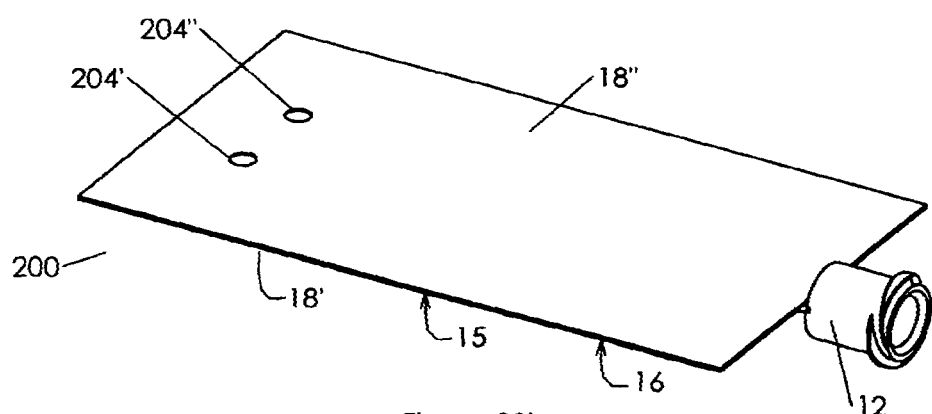

FIG. 20*b* shows a subsequent step of the manufacturing process of the cartridge 200. After the second compartment 16 (in this Figure at the opposite side of the cartridge 200) has been filled and is hermetically sealed with a lid web 18". The web 18" is sealed to the entire uninterrupted surface of the first wall 18'. In one arrangement, the inner layer of the first web 18' and/or the second web 18" comprises an adhesive with controllable peeling (adhesion) force, where a lower sealing temperature (for instance 375° F.) results in a peelable adhesion ("frangible seal"); and a higher sealing temperature (for instance 450° F.) results in a permanent non-peelable adhesion. In one arrangement, at the first sealing step shown in this Figure, substantially all of the uninterrupted surface of web 18' is adhered to the second web 18" to form a frangible seal which completely circumference the second compartment 16, and substantially circumference the first compartment 15, with the exception of the filling channels 202' and 202". With the second web 18" now attached to the first web 18' a filling compartment and exhausting compartments are now formed, communicating with the first compartment 15 via channels formed between the two webs.

The first filling hole 204' and the second filling hole 204" may be pre-formed in the second web 18" prior to its introduction to the first wall 18' by one of the means known in the art such as punching, die-cutting, and laser cutting. In one arrangement, the first compartment is filled with a first substance through the first filling hole 204' while the second filling hole 204" allows for evacuation of gasses from the first compartment 15 during filling. A filling source may be associated with at least one of the filling holes 204' and 204" during the filling process to facilitate the introduction of a substance to the first compartment, and drawing the gases through the exhaust compartment. In one arrangement, the filling coupler is a needle or a tube that is bent to reach into the first filling channel 202'.

In one arrangement, the filling coupler has a cylindrical tip with a diameter greater than that of the filling hole 204' such that it tightly fit and liquid tight seals when introduced to the filling hole 204'. In one arrangement, the filling holes 204' and 204" are not pre-formed, and a sharp filling object (such as a hollow needle) pierces through the second wall 18" in a fluid tight fashion, into filling wells 201' and 201". This last arrangement is particularly beneficial as the package is hermetically sealed prior to the introduction of the constituent which can be performed on a different portion of the filling line or on a different line. The packages may be stacked between the sealing step and the filling step. In one arrangement, a rubber or semi rigid seal is disposed in at least one of the filling wells 201' and 201" forming an interface to the filling source to facilitate the sealing of the filling couplers to the cartridge. In one arrangement, the channels' cross section is sufficiently small to prevent the filled substance from spilling out of the first compartment 15, due to surface tension of the substance.

In one arrangement, a check-valve is disposed in at least one of the first and second filling wells 201' and 201" to control the flow of a substance into the first compartment 15. A semi permeable object may be disposed in one of the filling ports 201 and the filling channels 202, to allow gasses to escape during filling, and prevent the substance from leaving the first compartment 15. In one arrangement, the flow evacuating the first cavity 15 during filling is monitored and filling is discontinued when the evacuating fluid switches from gas to the filled substance. The first filling channel 204' is made such that the substance entering the first compartment is gliding on the second wall 18" and thus preventing jetting that may result in undesired bubbles or foaming of the filled dose. A dedicated flow deflector may be disposed in the filling channel 202 or the filling well 201 to facilitate the gliding of the filled substance on the wall of the first compartment 15.

Figure 20C:
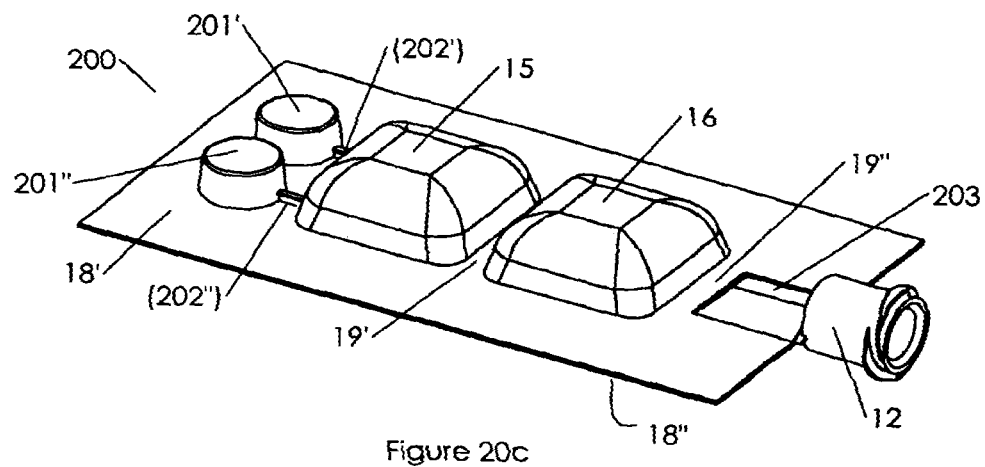

FIG. 20*c* shows a subsequent step of the cartridge 200 manufacturing. In a second welding step the channels (202') and (202") are depressed and welded, completely sealing the first substance in the first compartment 15. The sealing temperature may be higher than the frangible seal welding temperature to avoid rupture of the channels (202') and (202"). In one arrangement, this sealing step is further applied to the circumference of the cartridge 200, applying permanent seal properties to at least some of the areas that were earlier sealed as a frangible seal. A sealable insert may be disposed in the channels to facilitate welding and sealing of the channels.

Figure 20D:
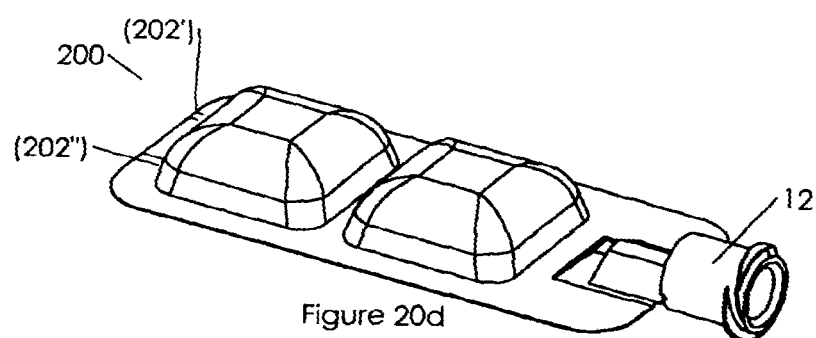
Figure 20E:
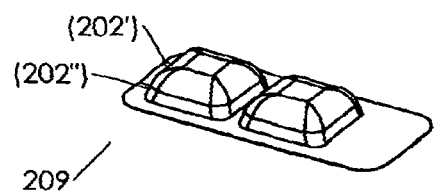
Figure 20F:
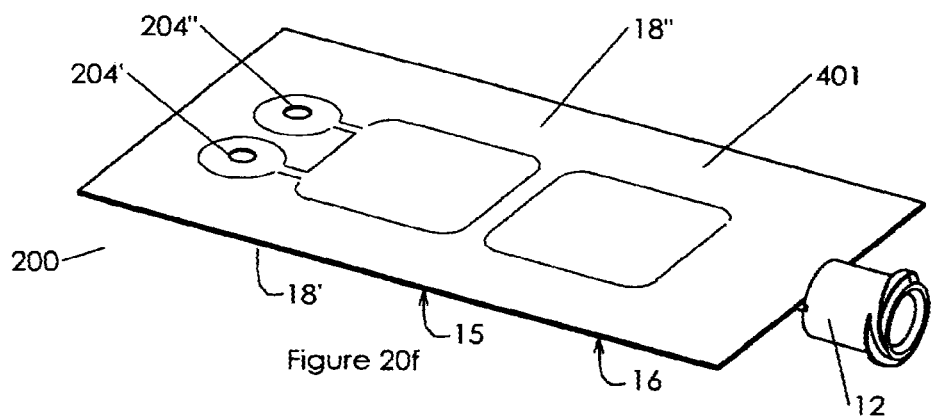
FIG. 20f is showing the frangible seal pattern 401
Figure 20G:
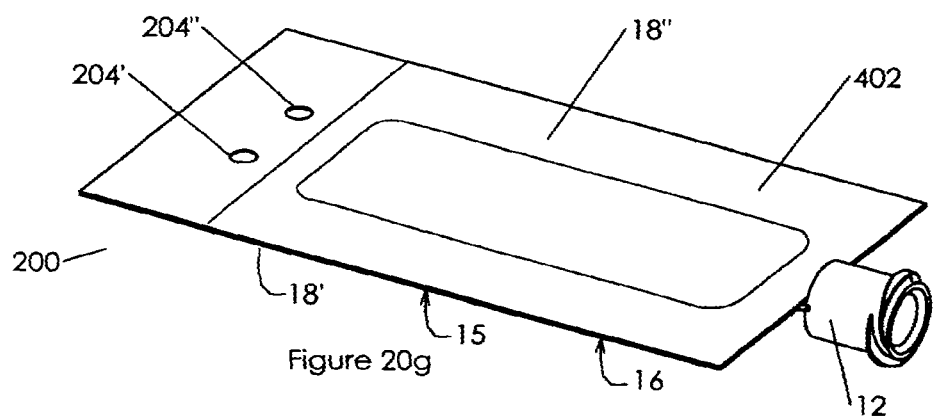
FIG. 20g is showing the permanent seal pattern 402 partly overlapping the frangible seal

Referring now to FIG. 20*d* the cartridge is trimmed from the web margins by one of the means known in the art including punching, ruler steel cutting, laser cutting, etc.

It would be understood to those skilled in the art that the manufacturing steps order disclosed above may be switched over in whole or in part to best suit a particular design, application, and manufacturing equipment.

The fitment 12 is welded to and between the first wall 18' and the second wall 18" prior or during the frangible seal welding step, prior or during the permanent seal welding step, or at a subsequent step by one of the fitment welding means known in the art including, for example, heat stake welding, impulse welding, vibration, ultrasonic, RF welding, and light beam welding.

Figure 21A:
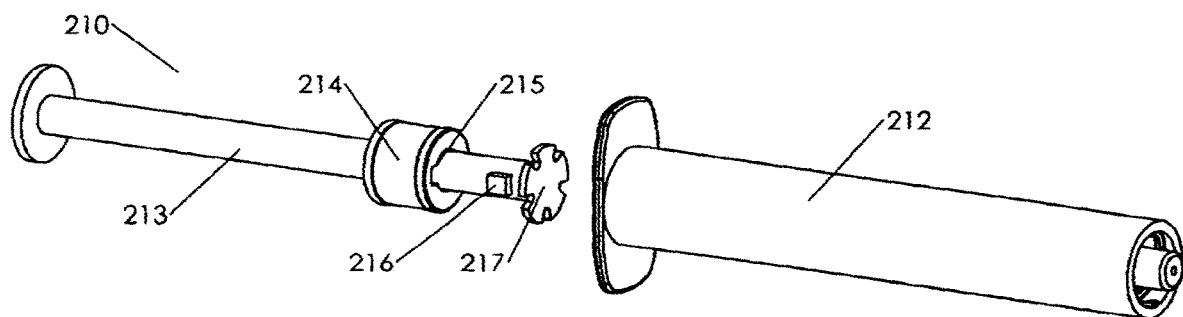
FIGS. 21a to 21e illustrate a syringe comprising a static mixing for mixing a substance contained in a syringe with a substance contained in a cartridge.

FIG. 21*a* shows an exploded view of a syringe 210 comprising a static mixer for mixing substances. In one arrangement, a first substance is contained in the syringe 210 and a second substance is transferred from a cartridge (not shown) to the syringe, where it is mixed with the first substance. In another arrangement, at least a first substance and a second substance are transferred to the syringe from one or more cartridges (or from a different source of the substance), separately or pre mixed, where a mixture process is applied to said substances or mixtures. In some arrangements, a cartridge is associated with the syringe 210 in a similar fashion to that of the arrangements of FIG. 2,3,4, 13 or 14. A plunger 214 is moveably disposed in the syringe barrel 212, in a fluid tight fashion. A piston 213 is concentrically disposed in a movable fashion in the annular bore of the plunger 214 in a fluid tight fashion; the piston further comprises a static mixing plate (or static mixer) 217, laterally extending from the distal end of the piston 213. A local axial groove 215 in the annular bore of the plunger 214 is made to receive laterally protruding detent tooth 216 of the piston 213.

Figure 21B:
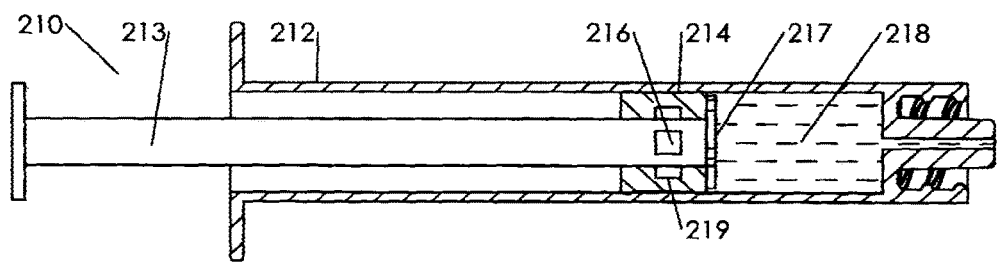

FIG. 21*b* shows a section view of the mixing syringe 210 containing a first substance 218.

Figure 21C:
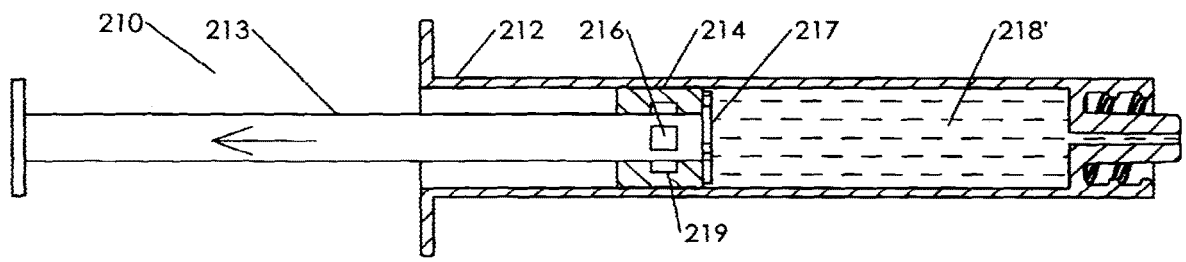

FIG. 21*c* shows a section view of the mixing syringe 210 where the piston is retracted toward the proximal end of the barrel 212. The static mixer pushes the plunger the plunger along with the piston allowing a second substance to enter the barrel 212 to form mixture 218'. The source of the second substance is not shown, however as described above it may be a cartridge associated with the syringe 210 in one of the arrangement provided in this disclosure. It is understood that if the second substance is not entering the syringe 210 from the Luer tip, the Luer tip is sealed with a cap, a closure, a valve or another means such that no flow from the tip occurs during the piston retraction.

Figure 21D:
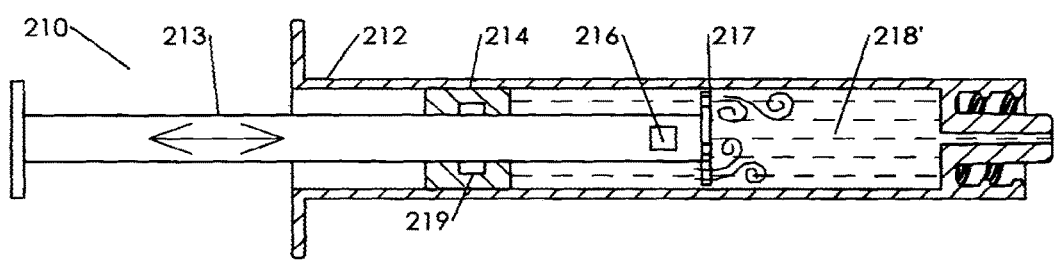

FIG. 21d shows a mixing step where the piston 213 is moved back and fourth diverting the mixture 218' to flow through the openings in the static mixer 217 and enhance the mixing of the mixture 218' to form a homogeneous product. The detent tooth 216 is aligned with the axial groove 215 (not shown) such that the piston is freely movable relative to the plunger 214. The plunger is free to glide along the barrel and compensate of the piston's stem as it moves into and out of the sealed volume between the barrel 212 and the plunger 214. In one arrangement, the piston is rotatable to further enhance the mixing. In one arrangement, the static mixing plate is replaced with another static mixer known in the art such as a porous material. In one arrangement, the piston is operated by a device such as a controlled electric actuator. The syringe tip and other ports to the syringe are preferably tapped during the mixing process to avoid mixture 218' spillage or introduction of materials into the barrel 212.

Figure 21E:
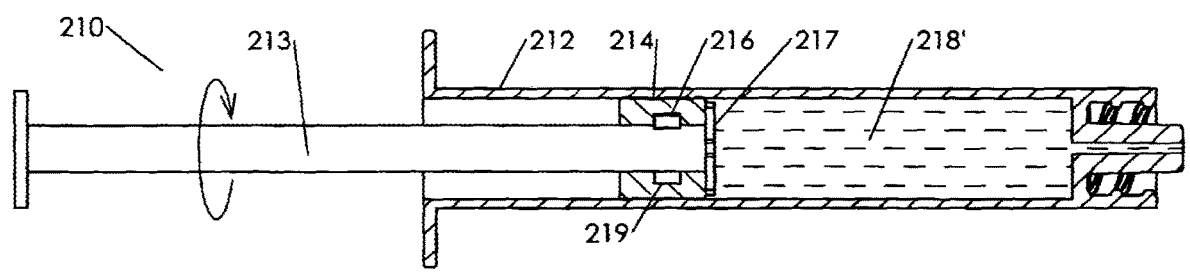

FIG. 21e shows the syringe 210 as the piston is retracted, such that the detent tooth 216 enters axial groove 215 (not shown); and the piston is rotated such that the detent tooth 215 engages with the radial groove 219 of the plunger 214, at which position the plunger 214 and the piston 213 are firmly engaged and are moveable as one. In one arrangement, the barrel and plunger comprise a non axi-symmetric cylindrical profile to prevent the rotation of the plunger due to the piston 213 rotation. In one arrangement, the plunger 214 comprises a rigid core to facilitate the engagement with the piston 213. As the syringe's 210 tip is untapped, the mixture 218' is dispensed by advancing the piston 213 and plunger 214 toward the distal end of the syringe 210.

Figure 22A:
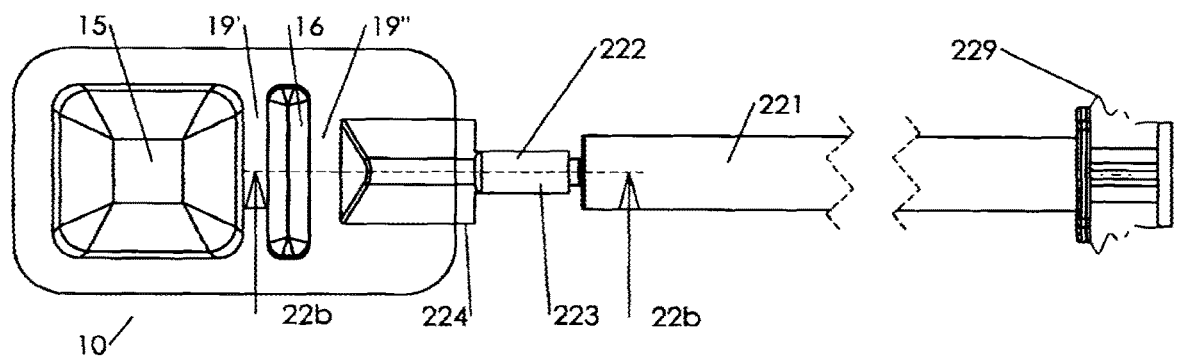
FIGS. 22a and 22b illustrate a cartridge communicating with a staked needle syringe via a fitment.
Figure 22B:
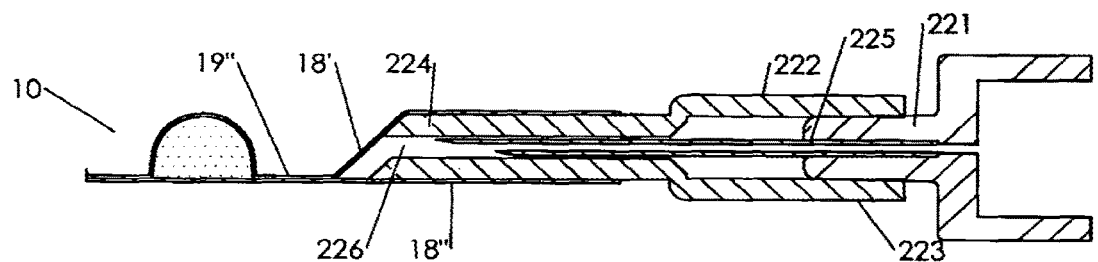

FIG. 22a, and the partial cross-section in FIG. 22b, illustrate a cartridge associated with a staked needle syringe. The cartridge 10 comprises a first substance compartment 15 and a second substance compartment 16 separated by a rupturable barrier 19'. The cartridge 10 further comprises a fitment 222, for communicating the content of the cartridge 10 with a staked needle syringe 221. The proximal end 224 of the fitment 222 is sealed between the first wall 18' and the second wall 18" of the cartridge 10, and is separated from the second compartment 16 by a rupturable barrier 19", formed by directly sealing the first wall 18' and the second wall 18". The distal end 223 of the fitment 222 is made to removably receive the tip of the syringe 221 in a fluid tight fashion; and the proximal end 224 of the fitment 222 is made to receive the tip of the needle 225, and protect it. A passageway 226 in the fitment 222 communicates between the needle and the content of the cartridge 10. The cartridge 10 provides an aseptic needle protector to the needle 225.

In one arrangement, the original needle protector (not shown) is removed from the syringe and is replaced by cartridge 10. The content of the cartridge 10 is transferred to the syringe 221 after the second barrier 19" has been ruptured. In some arrangements, the cartridge 10 is mounted on the syringe during the manufacturing process. In one arrangement, the cartridge 10 has only a single compartment. In one arrangement, the cartridge has at least two compartments that are merged prior to transferring the content of the cartridge 10 to the syringe 221. In one arrangement, the syringe 221 comprises a safety mechanism which, at the end of the injection, retracts at least a portion of the needle 225 to a position which protects from needle sticks. In one arrangement, the syringe 221 comprises a needle stick safety mechanism that at least partially protects the needle tip after the injection of the content has been completed.

Typically with pre-fillable syringes, the syringes are supplied to the filling process disassembled and the syringe is fully assembled after the content has been filled. The arrangement of FIGS. 22a and 22b provides for an advantageous manufacturing method whereby (a) the syringe 221 is supplied assembled and finished, (b) the cartridge 10 is filled and sealed with the desired content, and (c) the cartridge 10 is assembled. This process may be completed in an aseptic environment or the product may be terminally sterilized. Thus, the approach allows for producing a pre-filled syringe assembly which does not require the actual syringe components assembly. In addition, the cartridge, may be marked and labeled with the content information with our needing a special syringe label or package to provide this information. A label, or a portion of a label of the cartridge 10, may be transferable to the syringe, to maintain the product identification after the cartridge 10 has been removed.

FIGS. 22a and 22b illustrates the cartridge 10 with two mergeable substance compartments, however it would be obvious to those skilled in the art that the cartridge 10 may include merely one compartment on more than two compartments. The connection between the syringe 221 and the fitment 222 is shown as a fluid tight slip fit however other fitting features may be incorporated to facilitate the seal, the assembly, or the dismantle, including, for example, a thread, a helical ramp, a Luer fit, a Luer-Lock fit, an O-ring, a rubber seal component, an interlocking feature, a snap feature, other features known in the art to facilitate a fluid tight, removable connection, or a combination of the above. The distal end 224 of the fitment 222 may tightly fit around the needle 225, providing a fluid tight seal that prevents the content of the cartridge 10 from reaching to the space between said fitment 222 and the needle 225; and prevent air from reaching into the needle from that area. The fitment may be at least partially made from elastic material. It would be obvious to those skilled in the art that the fitment 222 may be designed such to accommodate the cartridge 10 in different orientations relative to the syringe, and in one arrangement the cartridge 10 and the syringe 221 may at least partially overlap or rest side by side. The syringe's 225 piston and barrel may be sealed at their proximal end by an aseptic membrane 229 such that the content contact surfaces will remain sterile without needling a sterile overwrap until the time of use.

Figure 23A:
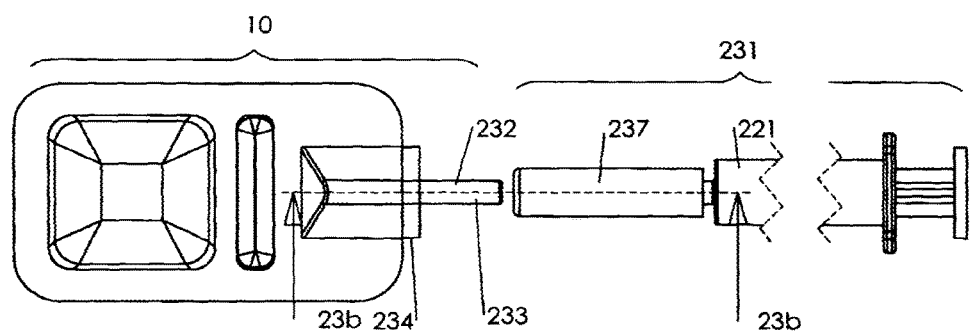
FIGS. 23a to 23f illustrate a cartridge and a staked needle syringe attachable via a coupler.
Figure 23B:
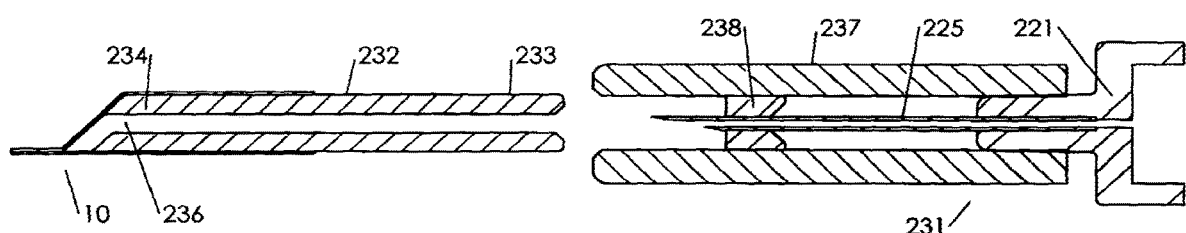

Referring to FIG. 23a and its scaled-up partial section view in FIG. 23b, another preferred arrangement of a cartridge and a staked needle syringe is illustrated. A staked needle adapter 237 is axially disposed around the needle 225 and is connected to the tip of the syringe 221 in a fluid tight fashion. The adapter 237 protects the needle from physical damage, and the operator and subject from accidental needle sticks. The distal end of the needle 225 is further supported by a centering glider 238, coaxially, movably disposed in the adapter 237 and around the needle 225. The fitment 232 of the cartridge 10 comprises a proximal section 234 attached to the cartridge walls, and a distal end 233 having an elongated cylindrical, that can be axially inserted to the syringe adapter 237. With this arrangement the needle 237 remains protected until the assembly with the cartridge 10.

Figure 23C:
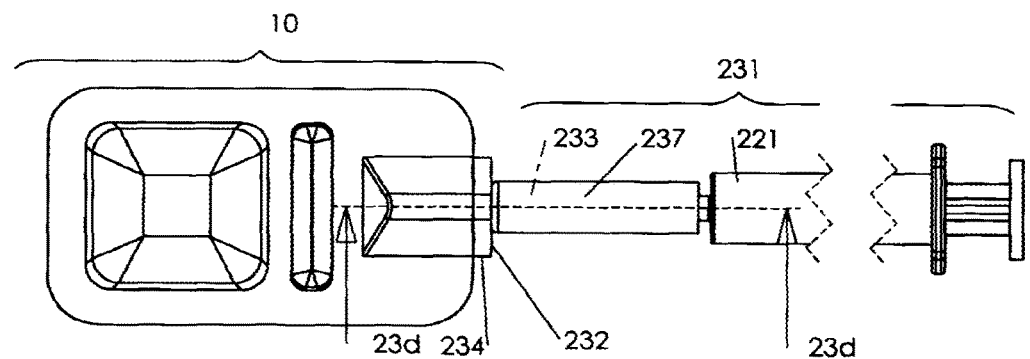
Figure 23D:
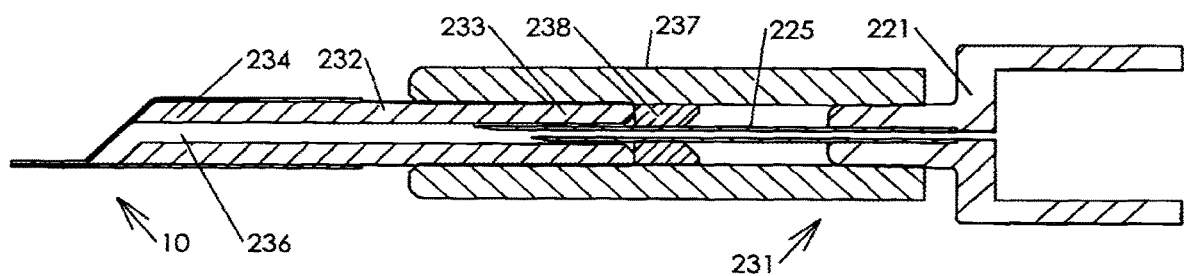

FIG. 23c and its scaled-up partial section view in FIG. 23d illustrates the arrangement of FIGS. 23a and 23b when the syringe assembly 231 and the cartridge assembly 10 are engaged. The distal end 233 of the fitment 232 is inserted into the adapter 237, pushing the centering piece 225 to expose substantial portion of the distal end of the needle which penetrates the fitment passageway 236, establishing fluid communication between the syringe 221 and the cartridge 10. A fluid tight seal may be provided by a tight fit between the needle 225 and the fitment 237. The fitment 237 may be at least partially made from elastic material to enhance the seal with the needle 225. The fitment 237 may further include a membrane sealing the distal end 233 or elsewhere along the passageway 236, further enhancing the seal between the fitment 237 and the needle 225, as well as further maintaining the cleanliness of the passageway 236 until it is assembled with a cartridge 10.

The content of the cartridge 10 is drawn into the syringe 221. Alternatively to the seal between the needle 225 and the fitment 237, a seal can be established between (a) the centering piece 238 and the adapter 237, (b) the centering piece 238 and the needle 225, (c) the syringe's 221 tip and the adapter 237, and (d) the fitment 232 and the adapter. In some arrangements, two substance compartments or more in the cartridge 10 are merged and allowed to mix before the content is transferred to the syringe 221. In some arrangements, substance in the syringe 221 is transferred and merged with a substance in the cartridge 10, before drawing the merged product. For example the cartridge 10 may contain a dry substance, and the syringe 221 may contain a dilutent; the dilutent is transferred tot the cartridge 10 and allows the powder to dissolve, and; the merged product is either transferred beck to the syringe, dispensed to a subject, or transferred to another device. In one arrangement, the syringe is prefilled with a substance, and the content of the cartridge 10 is transferred to the syringe 221, allowing it to merge with the substance in the syringe 221.

Figure 23E:
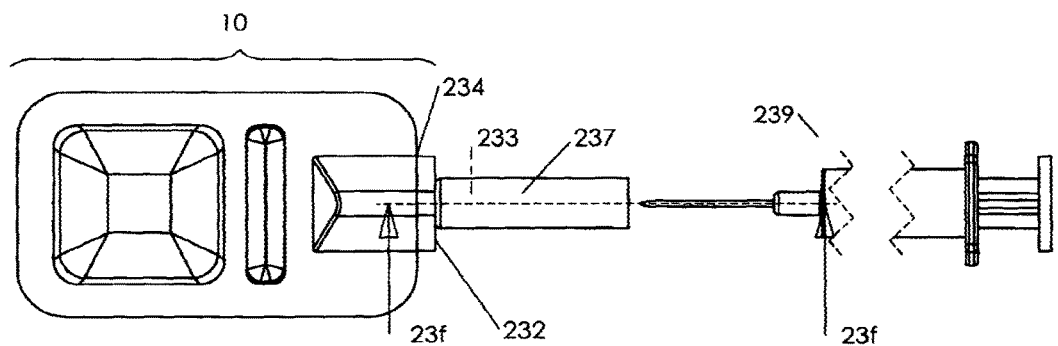
Figure 23F:
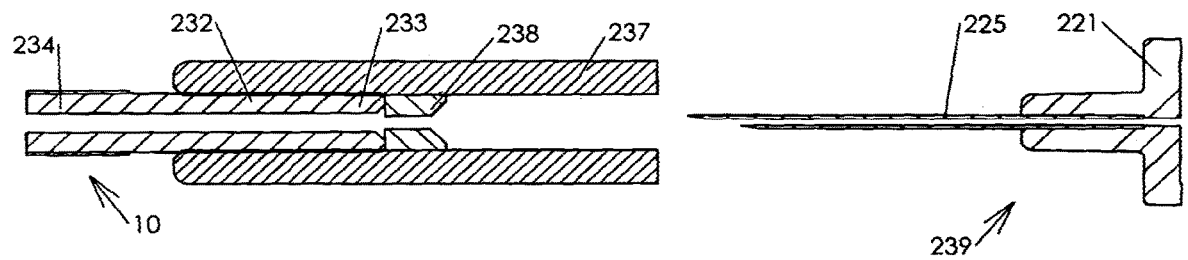

FIG. 23e, and its scaled-up partial section view in FIG. 23f, illustrates the arrangement of FIGS. 23c and 23d, when the cartridge is removed. The adapter 237 remains on the cartridge 10, and the needle is exposed as the syringe 221 is now ready for injection. In one arrangement, mechanical interlock ensures that the adapter 237 remains with the cartridge 10. Such mechanical engagement may include a thread, a helical ramp, a snap, a tight fit, or other engaging and disengaging features known in the art. In one arrangement, the adapter 237 remains on the syringe 221 when the cartridge 10 is removed, to continue providing protection to and from the needle 225; and it is removed prior to injection by the operator.

Figure 24:
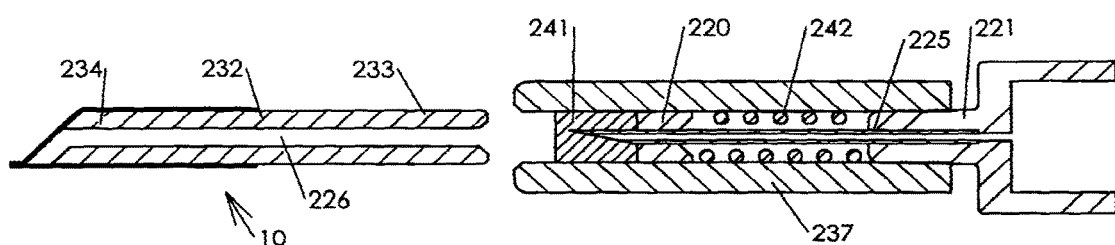
FIG. 24 illustrates another arrangement of a staked needle coupler.

FIG. 24 illustrates another arrangement similar to the arrangement of FIG. 23 with the exception that a rubber septum 241 is disposed on the tip of the needle, and a spring 242 biases the centering piece 220 and the septum 241 toward the distal end of the adapter 237. The needle is aseptically sealed by the septum 241. For transferring material between the cartridge 10 and the syringe 221, the distal end 233 of the fitment 232 is introduced into the adapter 237, displacing the septum and centering piece backward, and exposing the tip of the needle 225 to the passageway 226 in the fitment 232. When the cartridge 10 is removed, the spring 242 causes the septum to return to cover the tip of the needle 225, providing protection from mechanical damage and contamination to the needle 225 until the time of use. The adapter 237 is removed with the spring 242, the centering piece 220, and the septum 241 prior to use of the syringe 221.

Figure 25A:
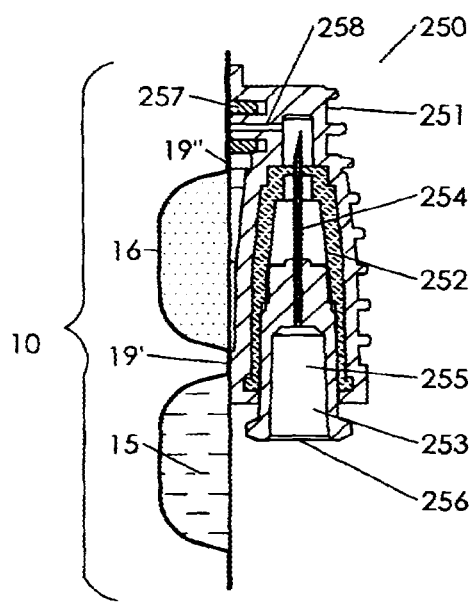
FIGS. 25a to 25c illustrate a cartridge comprising a coupler containing an injection needle

FIG. 25a illustrates a prefilled cartridge comprising a coupler 250 and a package associated via the fitment 257. The coupler assembly comprises a needle assembly 253 comprising a Luer Lock hub 255 and a stainless steel cannula 254 attached to the hub. The needle assembly (or needle) 253 is accommodated in a needle cap formed in the coupler 251. The coupler further comprises a fluid passageway 258 for communicating the needle 253 with the package 10. A rubber sheath 252 disposed in said coupler 251 forms an aseptic seal between the needle hub 255 and the coupler. The tip of the rubber sheath 252 forms a fluid tight closure of the fluid passageway 258, which is pierced by the cannula 254 to establish fluid communication between the needle 253 and the package. The Luer end 256 of the needle hub 255 is sealed with a removable aseptic closure either in the form of a sealed foil, a closure or other means known in the art. The package 10 comprises a first rupturable barrier 19' segregating between a first compartment containing a first constituent and a second compartment 16 containing a second constituent, said first and second constituents are allowed to merge when the rupturable barrier is ruptured. In another configuration, the package 10 comprises a single constituent of the beneficial agent. In yet another embodiment the package comprises at least a third compartment comprising a third constituent segregated from the second or the first compartments by a rupturable barrier. A second rupturable barrier 19" provides a closure between the second compartment 16 and the fitment 257 leading to the passageway 258 in the coupler 251.

Figure 25B:
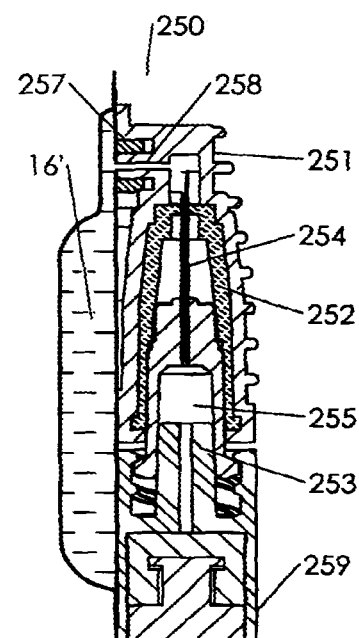
Figure 25C:
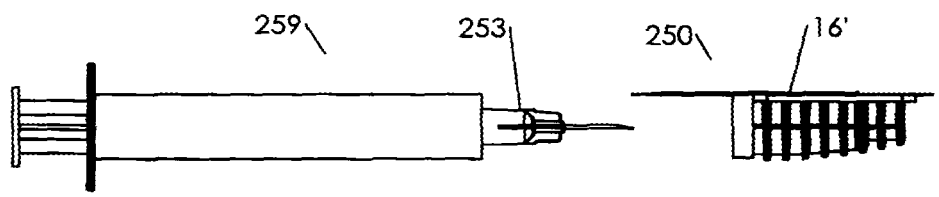
Figure 25D:
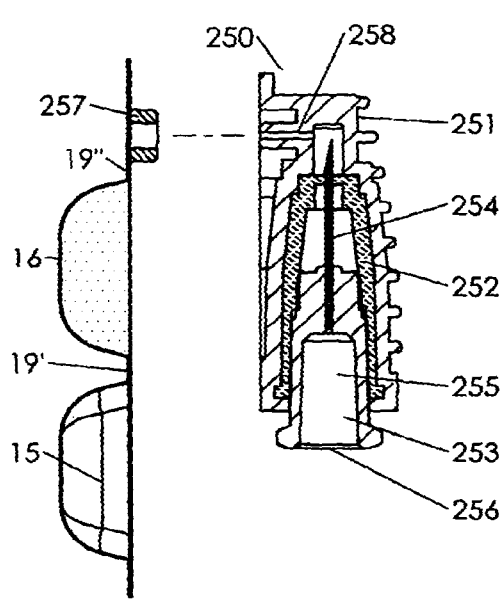
FIG. 25d is showing the two sub assemblies of the prefilled cap
Figure 25E:
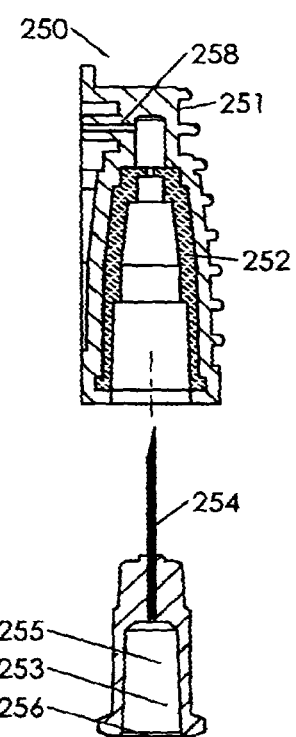
FIG. 25e is showing an exploded view of the cap portion of a cartridge

FIG. 25b illustrates the arrangement of FIG. 25a after the first and the second rupturable barriers have been opened, allowing the first and second constituents to merge, and establishing fluid communication of said mixture 16' with the needle 253 via the coupler 251. The arrangement provides a simple prefilled cartridge that can be mounted on a standard Luer syringe 259 via engagement of the female Luer connector of the needle 253 with the male Luer of the syringe 259. The product 16' can then be taken into the syringe by retracting the syringe's piston, which after the coupler may be removed to expose the needle 253 for injection as shown in FIG. 25c. In one configuration, the syringe may contain a third constituent that may be merged with the product 16' either by drawing the product 16' into the already partly filled syringe, or by first dispensing said third constituent from the syringe to the package 10 and secondly draw the mixture back to the syringe or to a different delivery device. The coupler 251 further provides a backing for part of the package 10.

Figure 26:
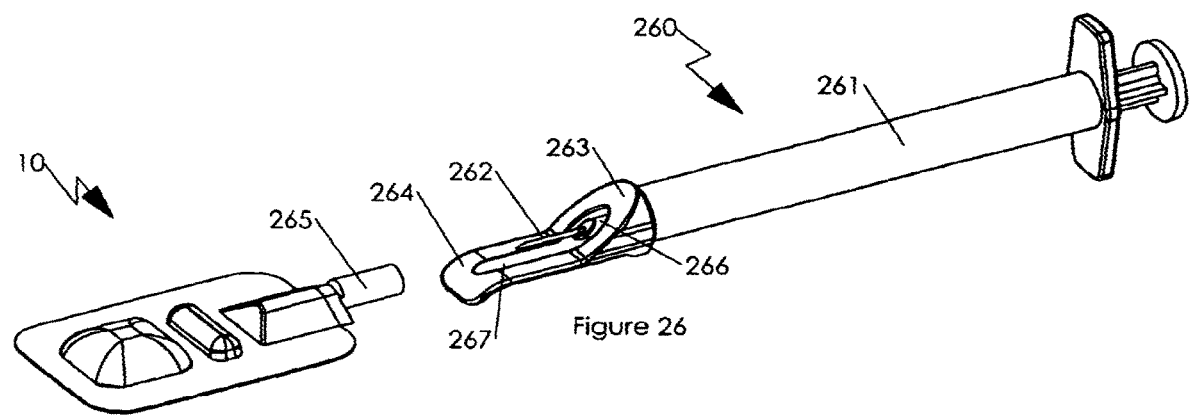
FIG. 26 illustrates the cartridge adopted for a syringe with an intradermal (ID) injection adapter

FIG. 26 illustrates a prefilled unit-dose aseptic reconstitution cartridge comprising a package 10 adopted to communicate with a syringe 260, comprising an intradermal (ID) injection adapter (ID Adapter), comprising a forwardly protruding skid 264 facilitating a shallow insertion of the needle 262 to the skin. US Pat. Publication Nos. 2010/0137831 and 2011/0224609 are teaching similar arrangement of an adapter to facilitate intradermal injection and are incorporated herein in their entireties by this reference. The ID adapter may be an integral portion of the syringe 261 or a clip on, forming an ID syringe. A recess 267 is formed in the skid 264 to facilitate the introduction of the fitment 265 of the package 10 onto the needle hub 266 of the syringe 260.

Figure 27A:
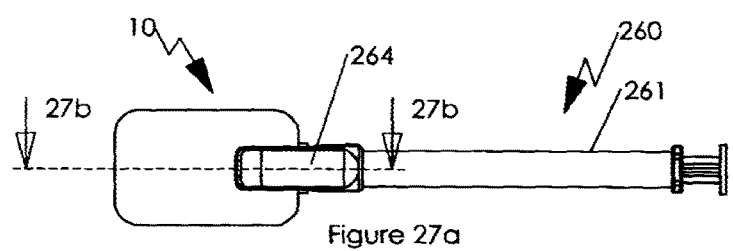
FIGS. 27a and 27b illustrate a cartridge associated with an ID syringe
Figure 27B:
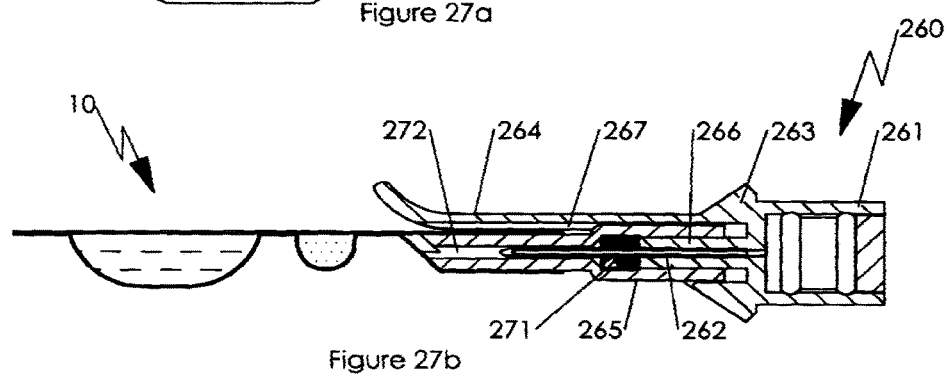

FIG. 27a illustrates the cartridge 10 mounted on an ID syringe where the cartridge 10 and syringe 260 are positioned in a linear arrangement. The view provides an orientation of the section view of FIG. 27b. FIG. 27b illustrates the fitment 265 press-fitted on the needle hub 266 forming an aseptic connection. A rubber stopper provides a closure to passageway 272 and is pierced by needle 262 to establish fluid communication between the syringe and the package 10.

Figure 28:
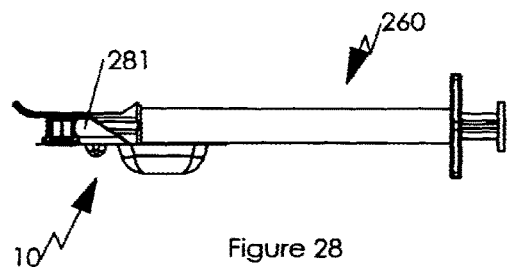
FIG. 28 illustrates another arrangement of a cartridge associated with an ID syringe

FIG. 28 illustrates a similar arrangement to that of FIG. 10 with the exception that the fitment 281 is made such that the package 10 is positioned parallel to the syringe barrel instead of in line with the syringe axis.

Figure 29A:
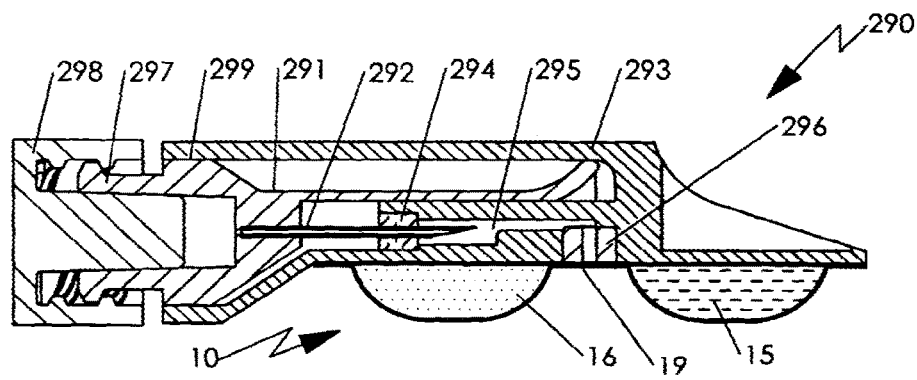
FIGS. 29a and 29b illustrate another arrangement of a cartridge comprising an ID needle arrangement
Figure 29B:
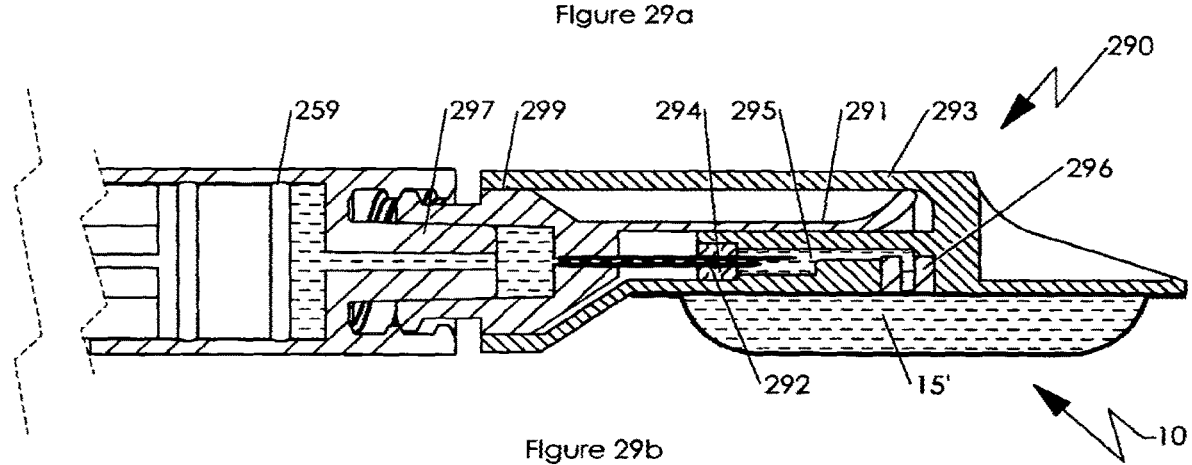

FIGS. 29a and 29b illustrates a cartridge configuration comprising a coupler 293 communicating an intradermal needle assembly 291 and the package 10. The coupler accommodates a needle assembly comprising a cannula 292 and a needle hub 291 comprising the forward protruding skid at its distal end and a Luer connector at its proximal end 297. The coupler 293 is used as an aseptic cap engaged with the needle hub 291 in sealing area 299 maintaining the needle 292 and the skid area sterile. A Luer cap 298 is aseptically sealing the Luer connector 297 of the needle hub 291 forming an integrally sealed cartridge which remains sterile without the need of a sterile overwrap. The package 10 and the coupler are connected via the fitment 296. The fitment is preferably heat welded to the wall of the package 10, and is connected to the coupler by one of the means known in the art including heat welding, bonding, or a tight mechanical fit. The rupturable seal 19 between the first compartment 15 and the second compartment 16 provides a closure segregating said compartments from the coupler 293.

FIG. 29b illustrates the arrangement of FIG. 29a where the Luer cap 298 is replaced with a Luer syringe 250, the rupturable seal is opened allowing the constituents in the first and second compartments 15,16 to merge and establishing fluid communication with the needle via passageway 295. The rubber closure 294 limits the dead space of the constituents in the coupler to the minute volume of passageway 295, thus limiting waste of the product 15'. The Figure is showing the piston of the syringe retracting to receive the product 15' in the syringe's barrel. The coupler is removed to expose the needle and the ID adapter for injection. The coupler 293 provides a backing to the package 10 facilitating depression of the compartments of the package 10.

Figure 30:
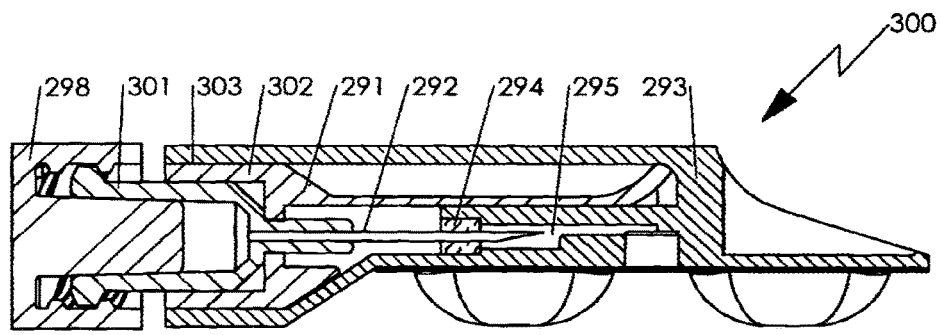
FIG. 30 illustrates another arrangement of a cartridge comprising an ID needle arrangement

FIG. 30 illustrates a cartridge arrangement 300 similar to the cartridge arrangement 290 of FIG. 29 with the exception that the ID adapter 291 is mounted on a needle hub 301. The needle hub 301, the ID adapter 291 and the coupler 293.

Figure 31A:
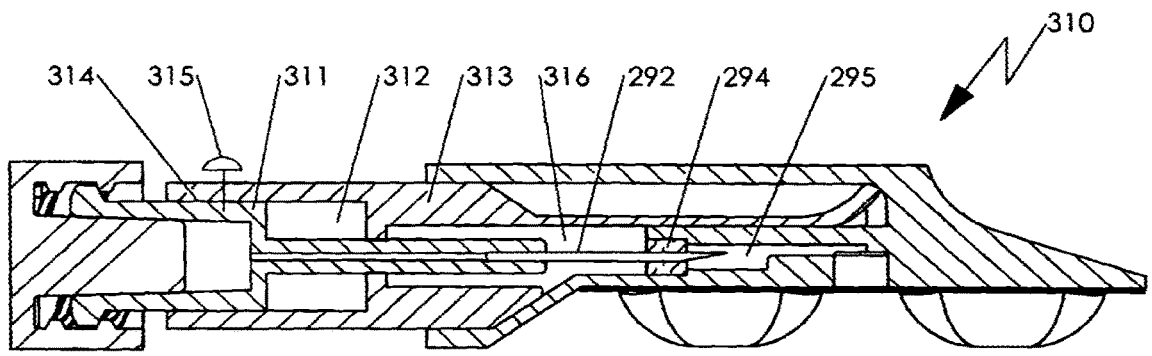
FIGS. 31a and 31b illustrate a cartridge comprising a needle safety and disabling features.
Figure 31B:

FIG. 31a shows a cartridge 310 having an arrangement that is mostly similar to the arrangement 300 of FIG. 30 with the exception that the needle hub is moveably disposed in the ID adapter 313, moveable between an injection position and safe-discard position. A latch mechanism 315 retains the injection position. A spring may be disposed in area 312 to bias the needle hub 313 to the safe-discard position. FIG. 31b illustrates arrangement 310 when the latch has been operated to release the needle hub. The needle assembly is retracted bringing the needle tip to a confined section 316 reducing the risk of needle sticks. In one arrangement the needle hub is permanently locked in this position to prevent repeated use of the needle.

Figure 32:
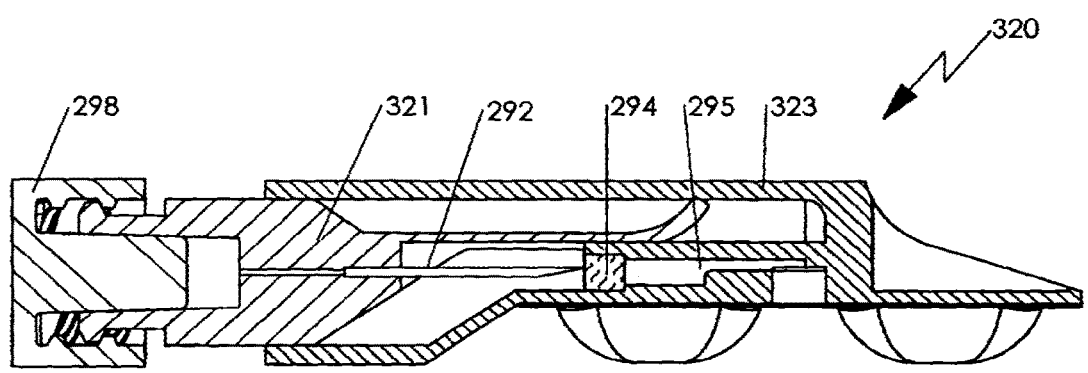
FIG. 32 illustrates a cartridge with a movable needle

FIG. 32 shows a cartridge arrangement 320 similar to arrangement 290 of FIG. 29 with the exception that the needle assembly is movably disposed in the coupler, and is moveable between a first position where the needle tip 292 does not pierce the stopper 294, or is only partly piercing the stopper, to a second position where the needle tip pierces the stopper to establish fluid communication with the fluid passageway 295.

Figure 33A:
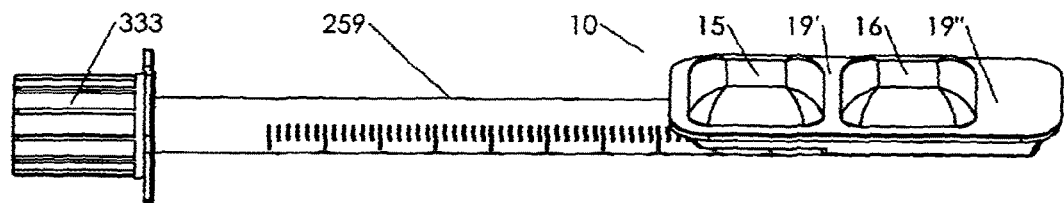
FIGS. 33a to 33e illustrate a prefilled syringe arrangement
Figure 33B:
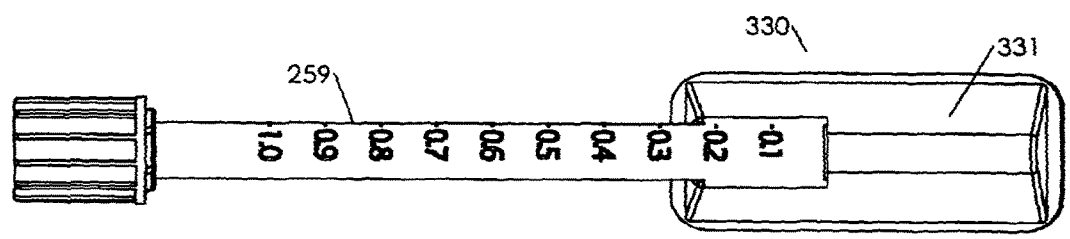
Figure 33C:
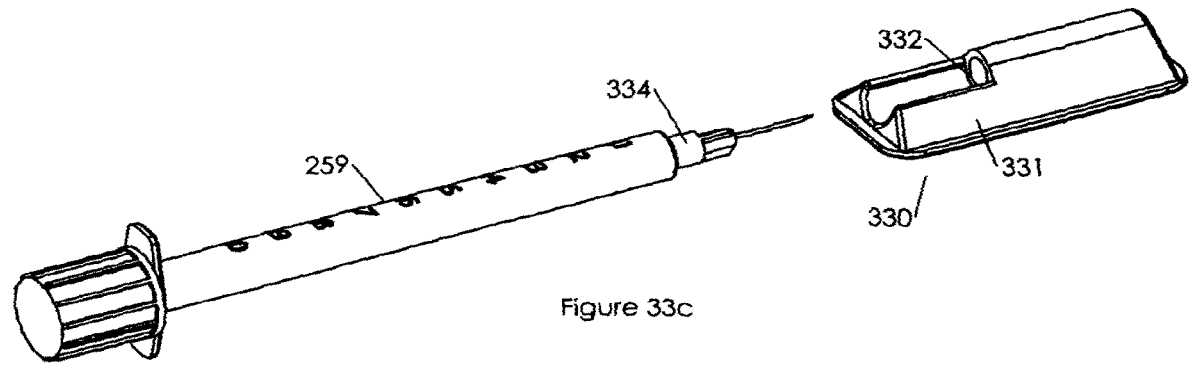
Figure 33D:
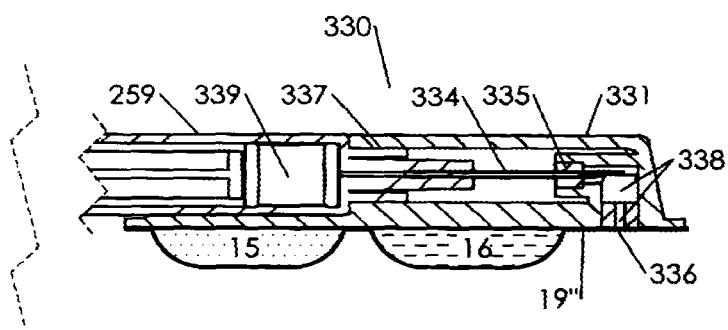
Figure 33E:
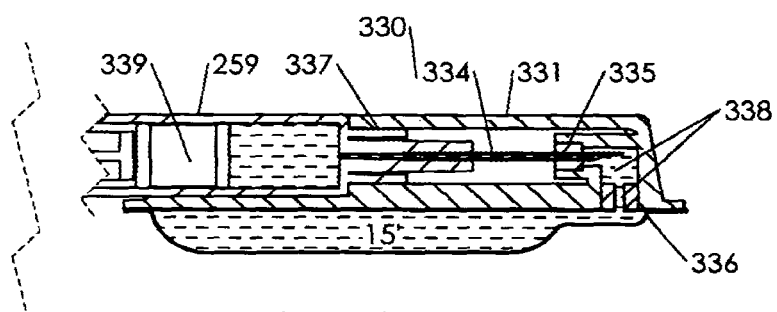
Figure 34:
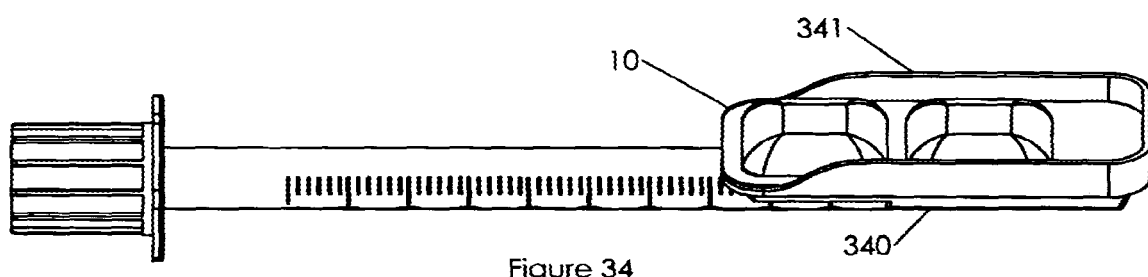
FIG. 34 illustrates a cartridge with a backing and walls protecting the prefilled package of the cartridge.

FIG. 33a to FIG. 33c illustrates a prefilled syringe 259 comprising a regular piston-and-barrel syringe arrangement with a staked needle 334 for delivering medication. A syringe cap 331 communicates with the syringe in an aseptic engagement. The cap 331 is engaged with a package 10 to form a removable cartridge 330. The body of the cap 331 operates as a coupler between the fitment of the package and the needle. FIGS. 33d and 33e show an scaled up section view of the cap during storage and after activation as the dose is being filled to the syringe's barrel. The cap comprises a rubber stopper 335 that is pierced through by the needle 334.

It would be obvious to those skilled in the art that similar configurations are operative with other needle arrangements known in the art including, syringe with catheter, needle with protective soft sheath, intramuscular (IM) needle, Subcutaneous (SQ) needle, Intradermal (ID) needle, microneedle, safety needles, retractable needle, irrigation needle, etc.

The syringe further comprises a an aseptic closure 333 to the barrel such that this syringe assembly maintains sterile without the need of a sterile overwrap.

FIG. 37 illustrates an arrangement similar to the arrangement of FIG. 33 with the addition of protective walls 341 vertically protruding to protect the package 10. It will be obvious to those skilled in the art that the protection of the package can be enhanced by further surrounding the package with additional wall, a flip-over cover associated with the wall 341, a slideable cover, etc.

The packages of the arrangements of this disclosure may carry any marking including printing, barcoding, RFID tags, embossment, and engraving to communicate desired information with a person or a device. The package may be extended to provide sufficient marking surface as needed.

A compression panel may be associated with the package to facilitate depression of at least one compartment of the package either to urge the rupture of a rupturable barrier, or to urge expression of the dispensable product from the package.

The arrangement and method described above is applicable for other injectors, or dispensers types such as the jet injector cartridge taught in FIG. 1 or other arrangements discussed in this document. In one arrangement, a retractable needle mechanism, retractable needle connector mechanism, or other needle safety mechanisms, and reuse disabling mechanism is incorporated with the mixing syringe mechanism described herein.

The cartridge arrangement of the present disclosure may be combined with several forms of delivery devices or applicators to facilitate a desired form of use. A compression panel or roller may be incorporated to facilitate an efficient expression of the cartridge's content.

The applications of the present invention are not limited to the syringe and jet-injector applications which are provided here by way of example, and the teachings described herein can be applied to other applications such as aseptic filling of micro-pump reservoir, intramuscular auto injectors, intradermal auto injectors etc.

What is claimed is:

1. A cartridge for use with a beneficial agent delivery device, said delivery device having a fillable reservoir, said cartridge comprising:
    a reconstitution unit dose package, comprising:
        a first compartment containing at least a first constituent of the beneficial agent;
        at least a second compartment containing at least a second constituent of the beneficial agent; and
        a fitment disposed on said package and configured to establish a fluid interface between said package and the fillable reservoir; and
    a coupler separate from the reconstitution unit dose package, the coupler configured to support at least part of the reconstitution unit dose package and provide a cap for receiving at least a delivery portion of the delivery device;

wherein at least one of the first compartment and the second compartment comprises a flexible wall having a pre-formed structure; and wherein the coupler provides an aseptic engagement between the package and the delivery device.

2. The cartridge of claim 1 wherein the delivery portion of the delivery device comprises one of a needle, a connector, or a nozzle.

3. The cartridge of claim 1 wherein said first compartment is segregated from said second compartment by a rupturable barrier.

4. The cartridge of claim 1 further comprising a foil layer peelable off at least one of the first compartment and the second compartment.

5. The cartridge of claim 1 further comprising a fluid passageway between said first compartment and said second compartment.

6. The cartridge of claim 5 further comprising a static mixer disposed in said fluid passageway.

7. The cartridge of claim 1 further comprising a fluid passageway between said package and the delivery device, and a static mixer disposed in the fluid passageway.

8. The cartridge of claim 1 further comprising a filling compartment in fluid communication with said first compartment via a fluid filling passageway.

9. The cartridge of claim 8 wherein said fluid passageway is sealable to prevent fluid communication between the filling compartment and the first compartment.

10. The cartridge of claim 8 wherein said filling passageway is configured to direct fluid along a first wall of said first compartment to prevent jetting.

11. The cartridge of claim 8 further comprising a gas evacuation chamber in communication with said first compartment via a fluid evacuation passageway, said fluid evacuation passageway having a gas-permeable, liquid-impermeable seal disposed therein.

12. The cartridge of claim 1, wherein at least a portion of said first compartment or said second compartment comprises a tubular construction.

13. The cartridge of 15 wherein the filling compartment is configured to form a fluid tight communication with a filling system.

14. The cartridge of claim 1, wherein a periphery of said first compartment is sealed to said reinforced backing and side walls of said first compartment extend in a direction generally perpendicular to said reinforced backing.

15. The cartridge of claim 1 wherein:

said first compartment comprises a flexible wall having a pre-formed structure; and said first compartment is moveable between a pre-formed state in which said pre-formed structure defines a fillable cavity configured to receive the beneficial agent and a second deformed state in which the volume is substantially depleted.

* * * * *